United States Patent
Adler et al.

(10) Patent No.: US 6,979,819 B2
(45) Date of Patent: Dec. 27, 2005

(54) PHOTOELECTRON EMISSION MICROSCOPE FOR WAFER AND RETICLE INSPECTION

(75) Inventors: David Adler, San Jose, CA (US); Matthew Marcus, Berkeley, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 0 days.

(21) Appl. No.: 10/017,262

(22) Filed: Dec. 14, 2001

(65) Prior Publication Data
US 2003/0111601 A1    Jun. 19, 2003

Related U.S. Application Data

(60) Provisional application No. 60/338,711, filed on Nov. 30, 2001.

(51) Int. Cl.[7] .................................... G01N 23/227
(52) U.S. Cl. ......................... 250/307; 250/306
(58) Field of Search ........................ 250/307, 365

(56) References Cited

U.S. PATENT DOCUMENTS

| | | |
|---|---|---|
| 4,453,086 A | 6/1984 | Grobman |
| 5,118,941 A | 6/1992 | Larson |
| 5,256,877 A * | 10/1993 | Czernuszka et al. ........ 250/310 |
| 5,286,974 A | 2/1994 | Walker et al. |
| 5,432,345 A | 7/1995 | Kelly |
| 5,444,242 A * | 8/1995 | Larson et al. ............... 250/305 |
| 5,796,101 A | 8/1998 | Haight et al. |
| 5,973,323 A | 10/1999 | Adler et al. |
| 6,252,412 B1 * | 6/2001 | Talbot et al. ............... 324/750 |
| 6,310,341 B1 * | 10/2001 | Todokoro et al. ........... 250/305 |
| 6,317,514 B1 * | 11/2001 | Reinhorn et al. ........... 382/147 |
| 6,465,781 B1 * | 10/2002 | Nishimura et al. ......... 250/306 |
| 6,717,145 B1 * | 4/2004 | Takagi et al. ............... 250/311 |
| 2001/0010357 A1 * | 8/2001 | Ose et al. .................... 250/311 |

OTHER PUBLICATIONS

E. Bauer, et al. Surface Studies by Low-Energy Electron Microscopy (LEEM) and Conventional UV Photoemission Electron Microscopy (PEEM); Jan. 1989, pp. 49-57; Fed. Rep. Of Germany.

* cited by examiner

*Primary Examiner*—John R. Lee
*Assistant Examiner*—Phillip A Johnston
(74) *Attorney, Agent, or Firm*—Okamoto & Benedicto LLP

(57) ABSTRACT

A method of inspecting and imaging substrates with an electron beam. The method can include a illuminating the substrate with a photon beam to cause photoemission of electrons. A low energy electron beam can be used to prevent or reduce positive charging of the substrate. Reflected electrons and/or emitted photoelectrons can be imaged to review or inspect the substrate.

1 Claim, 25 Drawing Sheets

PHOTOELECTRON EMISSION MICROSCOPE FOR WAFER AND RETICLE INSPECTION

This Application claims the benefit of U.S. provisional patent application No. 60/338,711, filed Nov. 30, 2001, by inventor David L. Adler, entitled "A Photoelectron Emission Microscope for Wafer and Reticle Inspection."

BACKGROUND OF THE INVENTION

As the semiconductor industry shrinks the size of features on integrated circuits, wafer fabs require higher-resolution techniques for inspecting silicon wafers and photomasks. Electron-beam tools for metrology, offline inspection, and even online inspection have reached the marketplace. These systems are conventional scanning electron microscopes in which an incident beam of high-energy electrons strikes the wafer, causing secondary and other electrons to leave the surface. The electrons are detected, and the systems create an image of the wafer surface.

Scanning electron microscopes in the prior art have attempted to solve the problem of charge control; i.e., preventing the accumulation of a positive charge on the surface of the wafer as secondary electrons leave the surface of the material. This is a difficult problem, and many approaches have been attempted.

SUMMARY OF THE INVENTION

The object of the current invention is to provide an inspection system with higher resolution and greater sensitivity to differences in materials. We disclose a novel photoelectron emission microscope for wafer and photomask inspection, as well as for inspection for other substrates. In this microscope, an incident beam of photons strikes the wafer, and photoelectrons (electrons emitted via the photoelectric effect) leave the surface. The microscope can create an image of the surface by focusing the photoelectrons onto a detector.

The incident photons in a photoelectron emission microscope typically have lower energy than the incident electrons in a secondary emission electron microscope. In a photoelectron emission microscope, the incident photons may have an energy of only about 5 eV, which is only slightly greater than the work function of the metal on the wafer or photomask. As a result, the photoelectrons emitted have much lower energy than the secondary electrons emitted in a conventional scanning electron microscope. The photoelectrons also have a much narrower range of energies, from a fraction of an eV to about 2 eV. The narrower range of energies in the photoelectrons gives this microscope a key advantage over a scanning electron microscope: lower chromatic aberration in the imaging optics. As a result of its lower chromatic aberration, a photoelectron emission microscope offers higher resolution than a scanning electron microscope.

A photoelectron emission microscope can distinguish between two materials more clearly than a scanning electron microscope, especially when the energy of the incoming photons lies between the work functions of two materials. For example, polycrystalline aluminum has a work function of about 4.15 eV, silicon about 4.8 eV. If the microscope illuminates a patterned wafer with 4.5 eV photons, the aluminum will emit photoelectrons, but the silicon won't. As a result, the image will offer excellent contrast: the aluminum will be white and the silicon will be black.

We disclose the use of a beam of low-energy electrons, in addition to the beam of photons, to prevent a positive charge from accumulating on the wafer surface as a result of the photoelectron emission. We show that it is possible to operate the microscope in a variety of useful imaging modes based either on photoelectrons, or on low-energy electrons reflected from the surface of the wafer, or on both photoelectrons and reflected electrons. Furthermore, we disclose a novel method of distinguishing between photoelectrons and reflected electrons based on their angular distributions.

This novel method of distinguishing between photoelectrons and reflected electrons in a photoelectron emission microscope also has advantages when applied in a dual-beam secondary electron emission microscope to distinguish between secondary electrons and reflected electrons. We therefore also disclose novel apparatus and methods for inspecting substrates with a dual-beam secondary electron emission microscope.

The use of a low energy beam and a dual beam system are both described in more detail in commonly assigned co-pending U.S. patent applications Ser. Nos. 09/854,332, filed May 11, 2001, and 09/579,867, filed May 25, 2000. These patent applications are hereby incorporated by reference as though fully set forth herein.

DETAILED DESCRIPTION OF THE PREFERRED EMBODIMENTS

This section describes inventions related to the following topics:
- a single-beam photoelectron emission microscope for inspecting wafers and reticles,
- methods of imaging and inspecting wafers or reticles with a single-beam photoelectron emission microscope,
- a "dual-beam" photoelectron emission microscope which contains an electron beam as well as a photon beam,
- methods of imaging a substrate with a dual-beam photoelectron emission microscope by detecting photoelectrons,
- methods of imaging a substrate with a dual-beam photoelectron emission microscope by detecting reflected electrons,
- methods of imaging a substrate with a dual-beam photoelectron emission microscope by detecting both photoelectrons and reflected electrons,
- a dual-electron-beam inspection system with means for filtering to select secondary electrons,
- methods of imaging a substrate with a dual-electron-beam inspection system which involve filtering to select secondary electrons,
- a dual-electron-beam inspection system with means for filtering to select reflected electrons,
- methods of imaging a substrate with a dual-electron-beam inspection system which involve filtering to select reflected electrons,
- methods of imaging a substrate with a dual-electron-beam inspection system which involve filtering to select scattered secondary and reflected electrons, and
- a method of identifying the chemical composition of a defect on a wafer or a reticle.

Single-Beam Photoelectron Emission Microscope for Wafer or Reticle Inspection

Figure 1:
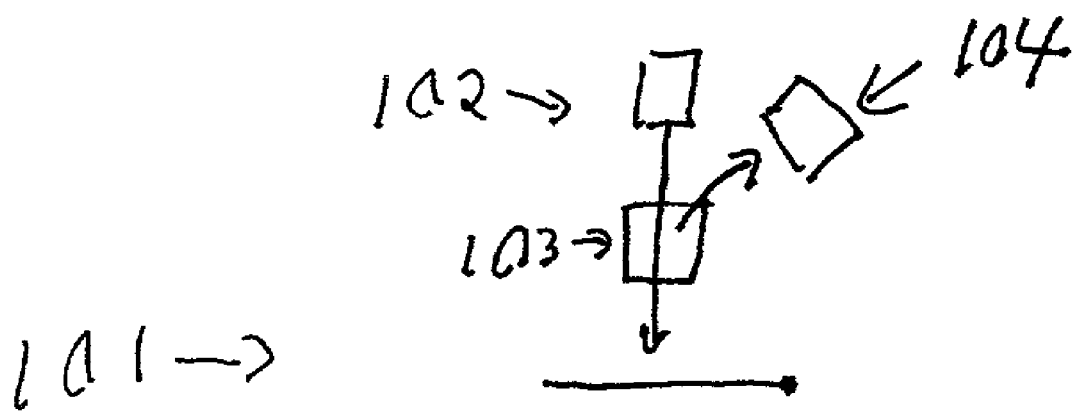
FIG. 1 shows a single-beam photoelectron emission microscope for imaging wafers or reticles.

The first invention which we disclose is a single-beam photoelectron emission microscope for imaging silicon wafers or reticles. A PEEM can offer lower chromatic aberration and thus higher resolution than scanning electron microscopes (which are conventionally used for wafer and reticle inspection) because photoelectrons have a much narrower energy spread than secondary electrons. FIG. 1 illustrates a photoelectron emission microscope (101) for wafer or reticle inspection. It includes three main components:
- a means (102) for exposing the wafer or reticle to an influx of photons with an energy sufficient to cause photoelectrons to leave the surface of the wafer or reticle,
- electron optics (103) for focusing the photoelectrons in the plane of a detector, and
- a means (104) for detecting the photoelectrons, thereby imaging a portion of the wafer or reticle.

The means (102) for exposing the wafer or reticle to an influx of photons could be a laser, an arc lamp, or any other light source which can emit photons with energy sufficient to cause photoelectrons to leave the surface of the wafer or the reticle.

The electron optics 103 used in this and any of the following embodiments may include various arrangements of lenses (such as electrostatic lenses, electromagnetic lenses, and combinations thereof). The electron optics shown in the commonly assigned cases previously incorporated by reference may also be used.

The means (104) for detecting the photoelectrons could be a diode, a back-thinned charge-coupled device such as a TDI sensor or any other electron-sensing device.

Figure 2:
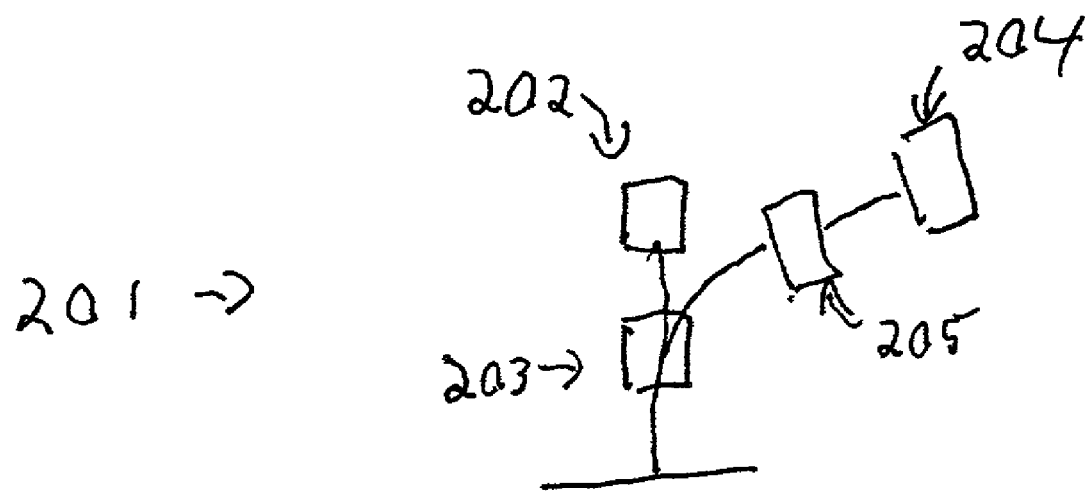
FIG. 2 shows a single-beam photoelectron emission microscope for inspecting wafers or reticles.

FIG. 2 shows a second embodiment of the photoelectron emission microscope (201) for inspecting wafers or reticles with higher image quality. It incorporates the three components already shown in FIG. 1:
- a means (202) for exposing the wafer or reticle to an influx of photons with an energy sufficient to cause photoelectrons to leave the surface of the wafer or reticle,
- electron optics (203) for focusing the photoelectrons in the plane of a detector, and
- a means (204) for detecting the photoelectrons, thereby imaging a portion of the wafer or reticle, and also a fourth component:
- a means (205) for converting the photoelectrons to photons before they strike the detector.

The means (205) for converting the photoelectrons to photons will improve image quality. It could consist of a scintillating material, a phosphorescent material, or any other material which will generate photons when struck by electrons. The detector 204 would then be a photodetector such as a CCD, TDI sensor, PMT, or any other suitable photodetecting element. The detector could be closely coupled to or integral with the scintillator. Means 205 preferably has a large gain.

Figure 3:
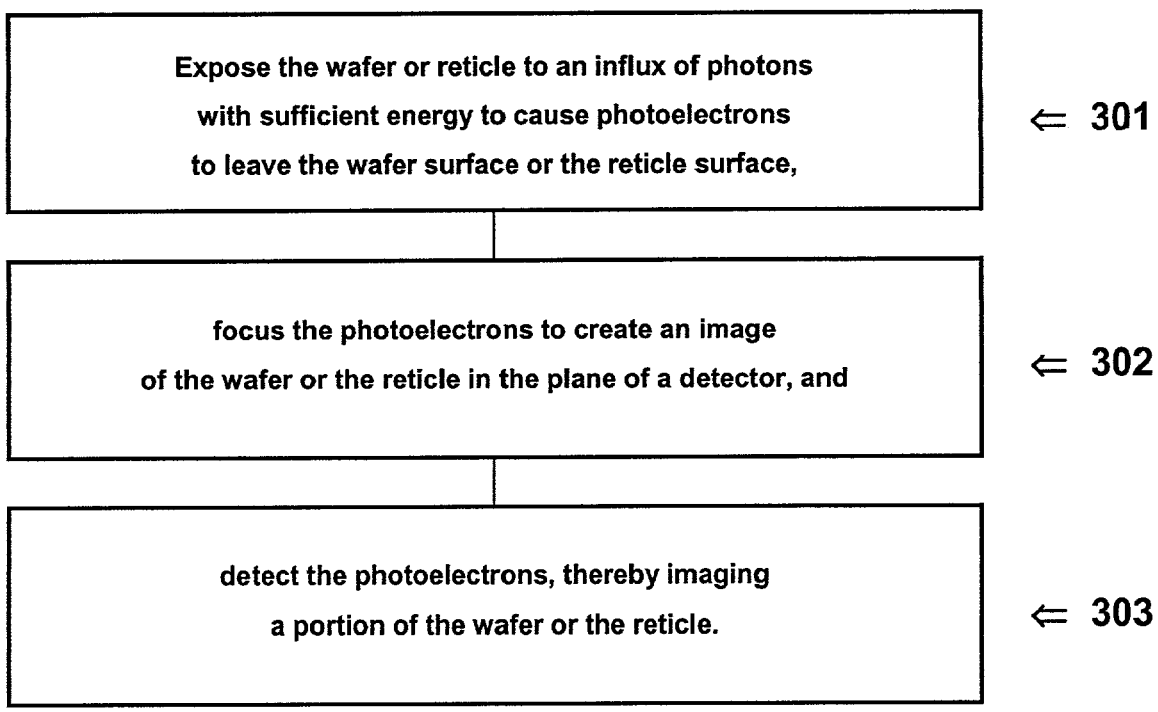
FIG. 3 illustrates a method of imaging a wafer or reticle with a single-beam photoelectron emission microscope.

Methods of Imaging and Inspecting Wafers or Reticles with a Single-Beam Photoelectron Emission Microscope FIG. 3 illustrates a method of imaging a wafer or reticle with a single-beam photoelectron emission microscope. It includes the following steps:
- exposing the wafer or reticle to an influx of photons with sufficient energy to cause photoelectrons to leave the wafer surface or the reticle surface (301), focusing the photoelectrons to create an image of the wafer or the reticle in the plane of a detector (302), and detecting the photoelectrons (303), thereby imaging a portion of the wafer or the reticle.

Figure 4:
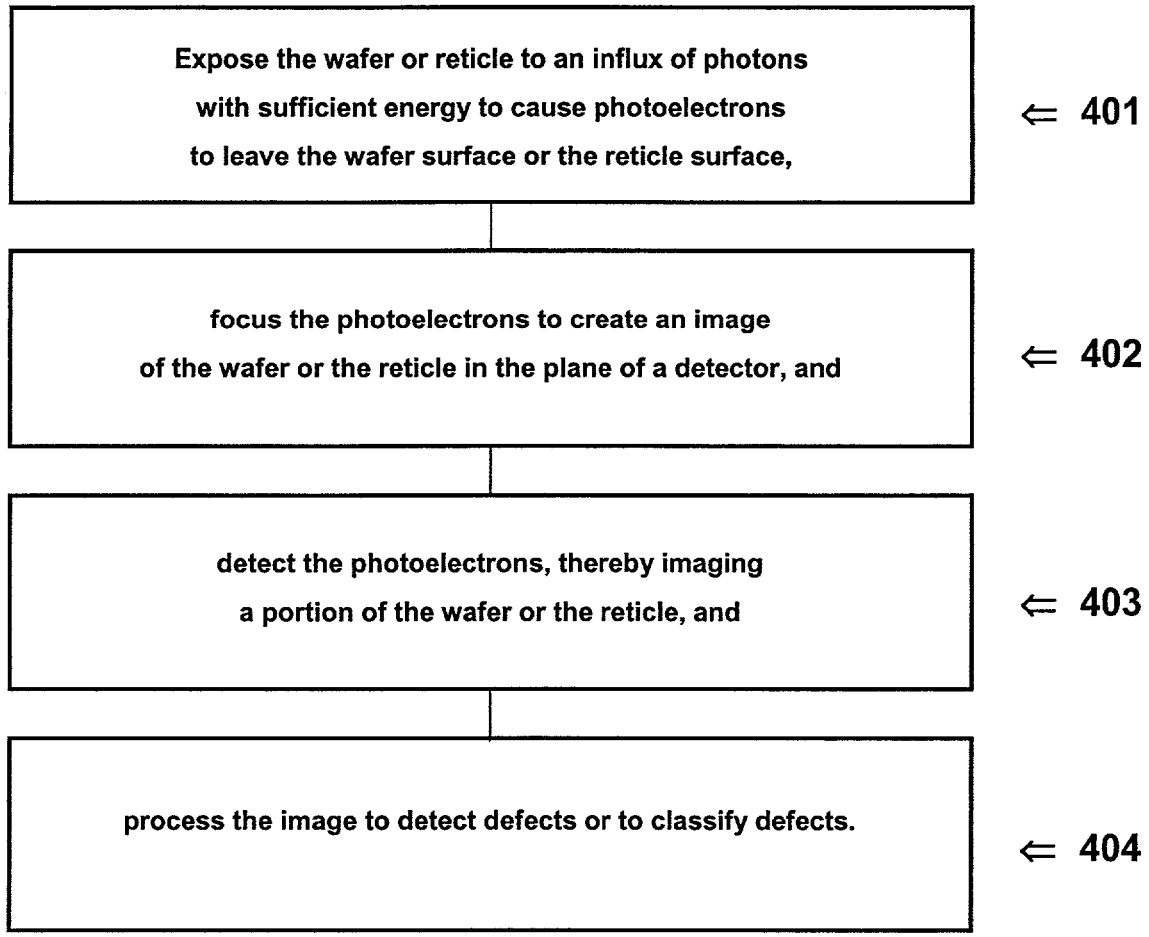
FIG. 4 illustrates a method of inspecting a wafer or reticle with a single-beam photoelectron emission microscope.

FIG. 4 illustrates a method of inspecting a wafer or reticle with a single-beam photoelectron emission microscope. It combines the three steps described above with reference to FIG. 3:

exposing the wafer or reticle to an influx of photons with sufficient energy to cause photoelectrons to leave the wafer surface or the reticle surface (401), focusing the photoelectrons to create an image of the wafer or the reticle in the plane of a detector (402), and detecting the photoelectrons, thereby imaging a portion of the wafer or the reticle (403), with the following additional step:

processing the image to detect defects or to classify defects (404).

In an important variant of the method shown in FIG. 4, at least two materials are visible on the surface of the wafer or the reticle, and the photons which strike the surface have an energy selected to increase the difference in photoelectron yield between at least two of the materials. For example, if the surface of a wafer contains both polycrystalline aluminum (which has a work function of about 4.15 eV) and silicon (which has a work function of about 4.8 eV), it would be useful to select a photon energy of 4.5 eV, in which case the aluminum would emit photoelectrons and the silicon would not. The image would offer excellent contrast, displaying the aluminum in white and the silicon in black.

In another variant of the method shown in FIG. 4, it is possible to vary the angle at which the influx of photons strikes the substrate. For the sake of design simplicity and for optimization of some imaging modes, it is useful to direct the influx of photons onto the substrate at a 90 degree angle. However, it is possible to increase sensitivity to topographic defects by directing the influx of photons onto the substrate at a smaller angle, even at a grazing angle such as 5 degrees or 10 degrees. Under these conditions, particles and other contamination shield the area of the substrate behind them from incoming photons. The shielded areas emit no photoelectrons and therefore appear in the acquired image as elongated shadows which clearly reveal the presence of defects. The smaller the angle between the influx of photons and the plane of the substrate, the larger the shadows cast by the defects.

When directing the influx of photons onto the substrates at an angle of less than 90 degrees, it is possible to optimize image contrast by polarizing the incoming flux of photons. For example, if the apparatus is directing the photons onto the substrate at an angle of, say, 10 degrees, and the influx of photons is horizontally polarized, then the electric field at the surface of the substrate will be very low. Since the photoemission rate is a function of the electric field at the surface of the substrate, the photoemission rate will also be very low. However, for particles or other features that rise above or dip below the planar surface of the substrate, the electric field will be high and therefore the photoemission rate will also be high. This strategy therefore delivers a high degree of image contrast for particle defects, which appear bright against a dark background. If, on the other hand, the influx of photons is vertically polarized, then the electric field at the surface of the substrate will be very high, and the photoemission rate will also be very high, creating a bright image.

Dual-Beam Photoelectron Emission Microscope for Imaging Substrates

Figure 5:
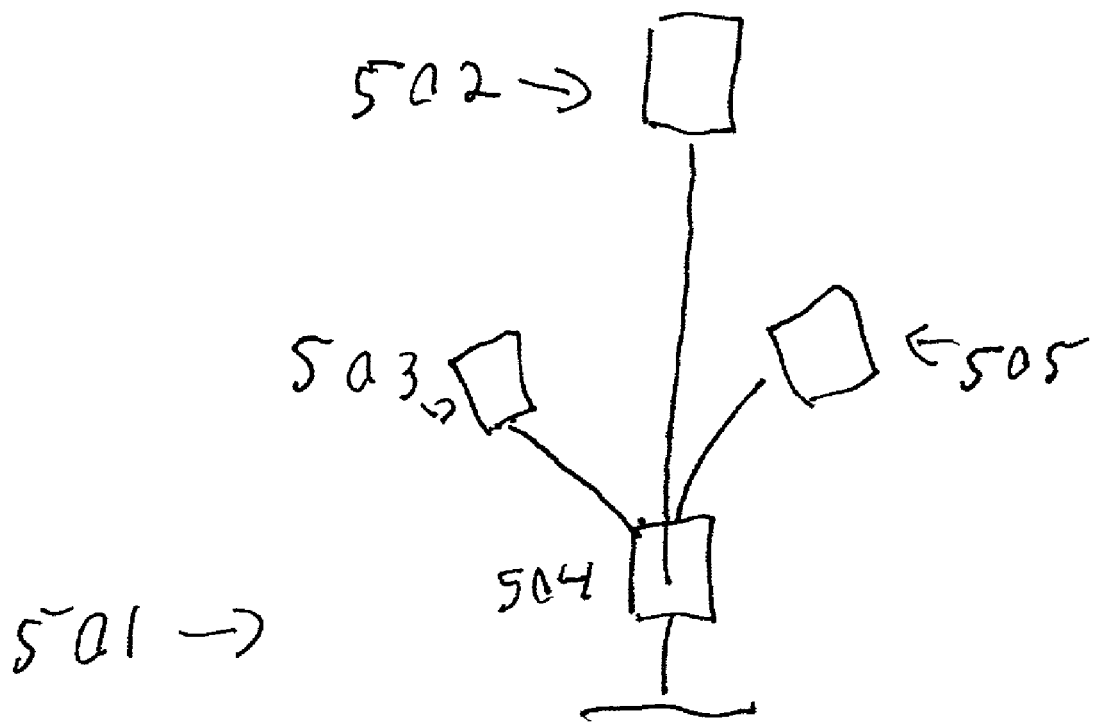
FIG. 5 shows a dual-beam photoelectron emission microscope.

One disadvantage of a single-beam photoelectron emission microscope is that as the negatively-charged photoelectrons leave the substrate being studied, a positive charge accumulates on the surface of the substrate. This residual charge can distort the image. To overcome this disadvantage, we disclose a dual-beam photoelectron emission microscope which illuminates the substrate with not only a photon beam, but also an electron beam, which prevents the surface of the material from accumulating a strong positive charge. FIG. 5 illustrates the simplest embodiment of this dual-beam photoelectron emission microscope (501), which includes four main components:

a means (502) for exposing the substrate to an influx of photons with an energy sufficient to cause photoelectrons to leave the surface of the substrate, a means (503) for exposing the substrate to an influx of electrons which have both an energy and a current density profile selected to maintain the surface charge present on the substrate at a predetermined level, electron optics (504) for focusing the photoelectrons in the plane of a detector, and a means (505) for detecting the photoelectrons, thereby imaging a portion of the substrate.

The means (502) for exposing the wafer or reticle to an influx of photons could be a laser, an arc lamp, or any other light source which can emit photons with energy sufficient to cause photoelectrons to leave the surface of the wafer or the reticle.

The means (503) for exposing the substrate to an influx of electrons could be an electron gun.

The means (505) for detecting the photoelectrons could be a charge-coupled device such as a TDI sensor or any other electron-sensing device, as described in more detail previously herein.

Figure 6:
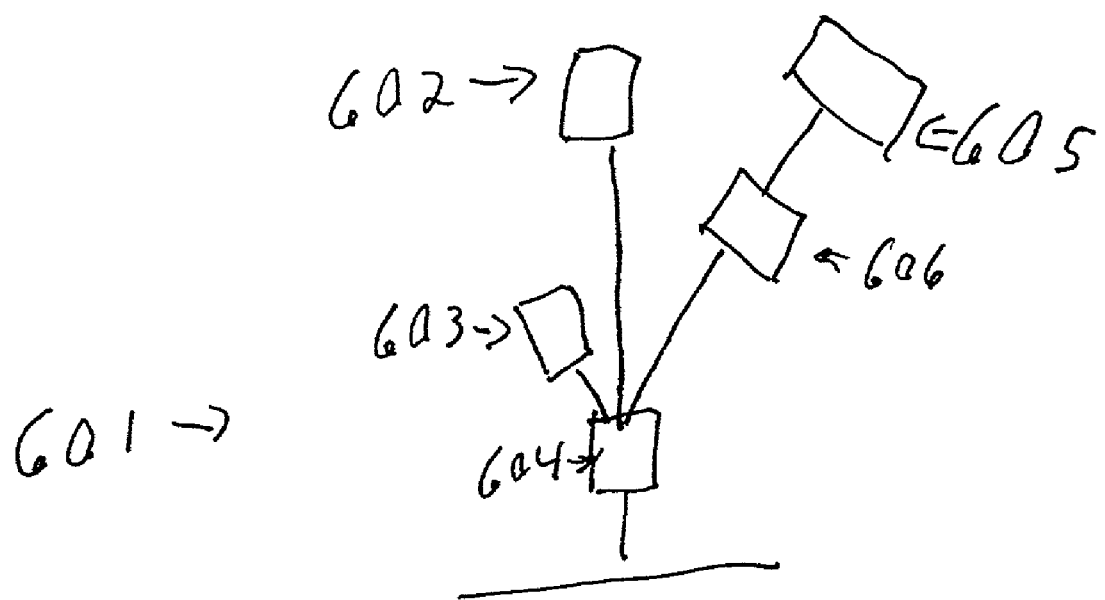
FIG. 6 shows a dual-beam photoelectron emission microscope which incorporates a means for converting the photoelectrons to photons before they strike the detector.

FIG. 6 shows a second embodiment of the dual-beam photoelectron emission microscope (601) for imaging or inspecting substrates with higher image quality. It incorporates the same four components as the embodiment already shown in FIG. 5:

a means (602) for exposing the substrate to an influx of photons with an energy sufficient to cause photoelectrons to leave the surface of the substrate, a means (603) for exposing the substrate to an influx of electrons which have both an energy and a current density profile selected to maintain the surface charge present on the substrate at a predetermined level, electron optics (604) for focusing the photoelectrons in the plane of a detector, and a means (605) for detecting the photoelectrons, with an additional fifth component:

a means (606) for converting the photoelectrons to photons before they strike the detector.

The means (606) for converting the photoelectrons to photons (thereby improving image quality) could include a scintillating material, a phosphorescent material, or any other material which will generate photons when struck by electrons, as described in more detail previously herein.

In the dual-beam photoelectron emission microscopes shown in FIGS. 5 and 6, the main purpose of the incoming electron beam is to prevent the substrate from gaining a strong positive charge. However, the substrate absorbs only a percentage of the incoming electrons. The remainder of the incoming electrons are reflected from the surface. These reflected electrons can strike the detector.

The microscopes shown in FIGS. 5 and 6 may actually generate an image created by a mixture of photoelectrons and reflected electrons. In some cases, it would be advantageous to create an image primarily with photoelectrons, which are particularly sensitive to material differences; in other cases, it would be advantageous to create an image primarily with reflected electrons, which are particularly sensitive to topography.

Figure 7:
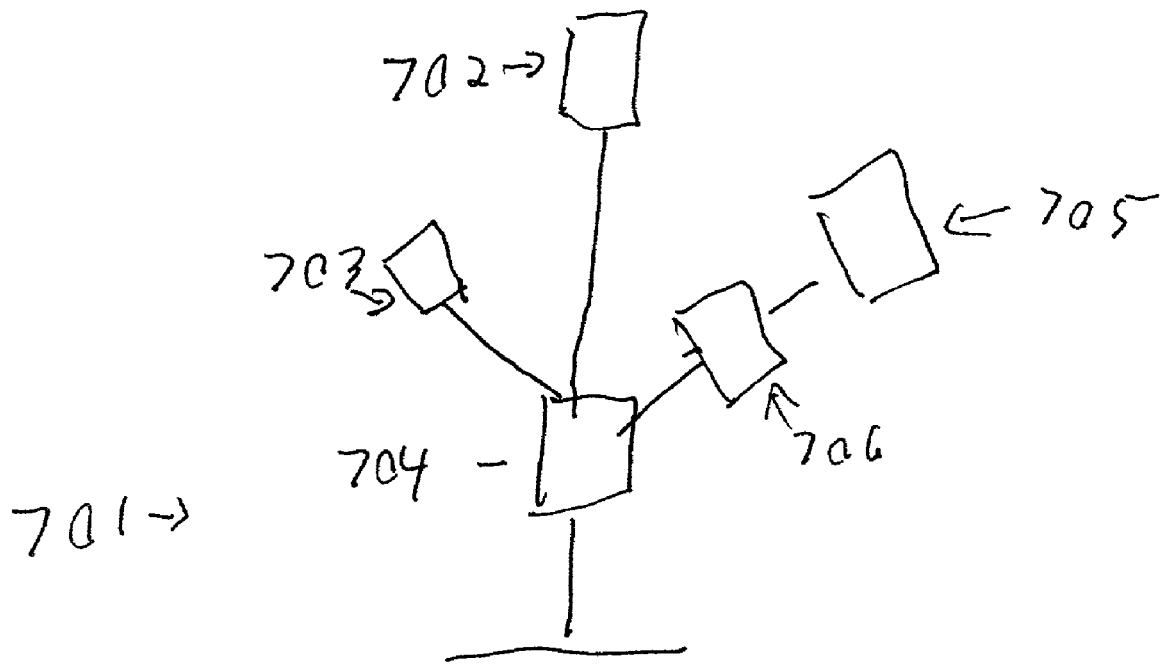
FIG. 7 shows a dual-beam photoelectron emission microscope (701) designed for imaging substrates primarily with photoelectrons.

Dual-Beam Photoelectron Emission Microscope for Imaging Substrates Primarily with Photoelectrons FIG. 7 shows a dual-beam photoelectron emission microscope (701) designed for imaging substrates primarily with photoelectrons. It incorporates the four components shown in FIG. 5:

a means (702) for exposing the substrate to an influx of photons with an energy sufficient to cause photoelectrons to leave the surface of the substrate,
  a means (703) for exposing the substrate to an influx of electrons which have both an energy and a current density profile selected to maintain the surface charge present on the substrate at a predetermined level,
  electron optics (704) for focusing the photoelectrons in the plane of a detector, and
  a means (705) for detecting the photoelectrons, thereby imaging a portion of the substrate, with an additional fifth component:

a means 706 for selecting said most or all of the photoelectrons, or a portion of the photoelectrons, and rejecting most or all of the electrons reflected from the substrate.

Figure 8:
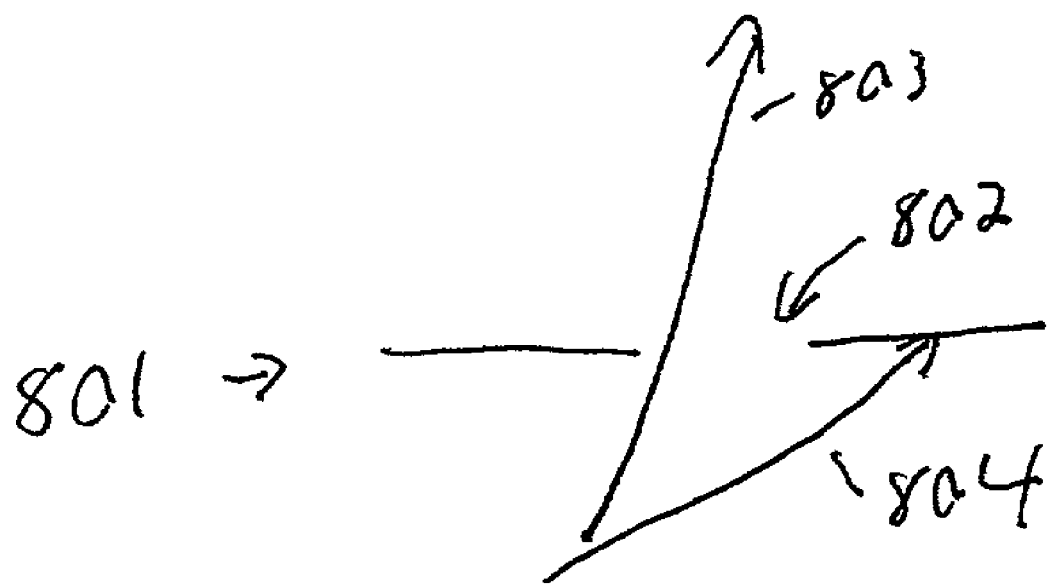
FIG. 8 shows a filter for selecting photoelectrons and rejecting reflected electrons.

This fifth component can consist of a filter which selects photoelectrons and rejects reflected electrons based on their angular distribution. FIG. 8 shows one specific example of such a filter 801, a blocking means containing a shaped aperture 802. Both photoelectrons and reflected electrons can leave the surface over a wide range of angles. However, their distribution peaks at different angles. Photoelectrons have the peak of their distribution at an angle normal to the substrate. Reflected electrons have the peak of their distribution at an angle of reflection which equals the angle of incidence. If we select an angle of incidence for the electron beam which is far enough from the normal, then the filter can select photoelectrons 803 and reject reflected electrons 804 based on their angular distribution.

Figure 9:
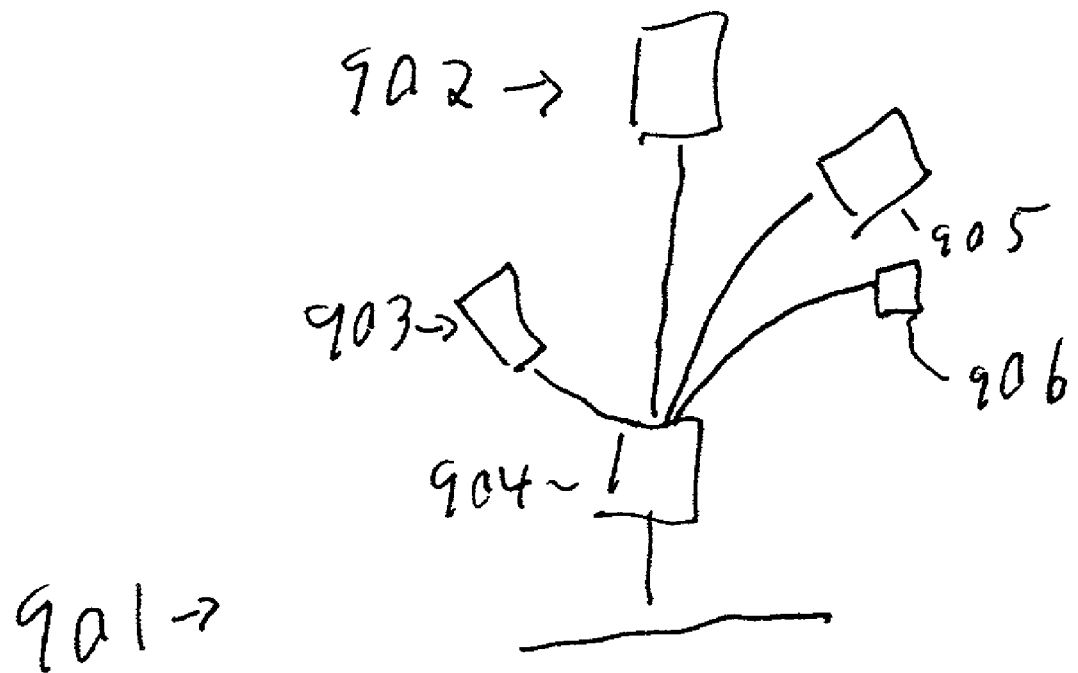
FIG. 9 shows a dual-beam photoelectron emission microscope designed for imaging substrates primarily with reflected electrons.

Dual-Beam Photoelectron Emission Microscope for Imaging Substrates Primarily with Reflected Electrons The presence of an electron beam, although primarily intended for charge control, gives us the opportunity to add an imaging mode based on reflected electrons. FIG. 9 shows a dual-beam photoelectron emission microscope (901) designed for imaging substrates with reflected electrons. It incorporates the four components shown in FIG. 5:

a means (902) for exposing the substrate to an influx of photons with an energy sufficient to cause photoelectrons to leave the surface of the substrate,
  a means (903) for exposing the substrate to an influx of electrons which have both an energy and a current density profile selected to maintain the surface charge present on the substrate at a predetermined level,
  electron optics (904) for focusing the photoelectrons in the plane of a detector, and
  means (905) for detecting the photoelectrons, thereby imaging a portion of the substrate, with an additional fifth component:

a means (906) for detecting electrons reflected from the surface of the substrate.

The means (906) for detecting reflected electrons could be a charge-coupled device such as a TDI sensor or any other electron-sensing device.

Figure 10:
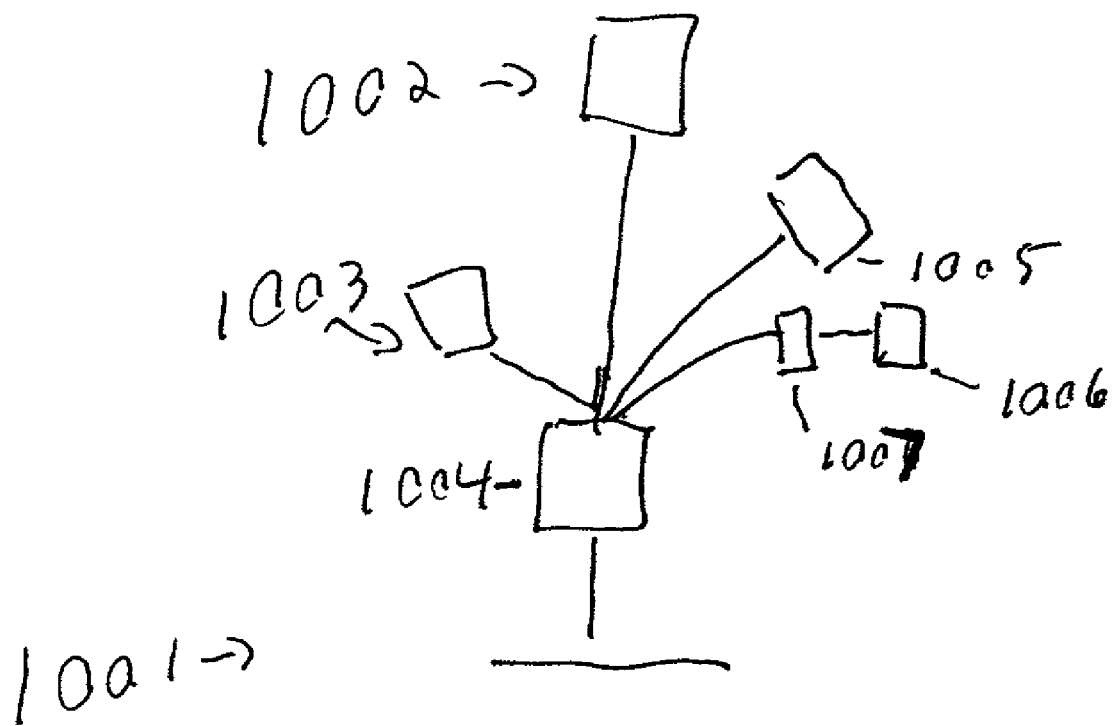
FIG. 10 shows a dual-beam photoelectron emission microscope with a means for converting the reflected electrons to photons before they reach the detector.

The dual-beam photoelectron emission microscope (901) shown in FIG. 9, like the novel devices described earlier, would achieve better image quality if it contained a means for converting the reflected electrons to photons before they reach the detector. FIG. 10 shows such a device, a dual-beam photoelectron emission microscope (1001) which incorporates the five components also shown in FIG. 9:

a means (1002) for exposing the substrate to an influx of photons with an energy sufficient to cause photoelectrons to leave the surface of the substrate,
  a means (1003) for exposing the substrate to an influx of electrons which have both an energy and a current density profile selected to maintain the surface charge present on the substrate at a predetermined level,
  electron optics (1004) for focusing the photoelectrons in the plane of a detector,
  a means (1005) for detecting the photoelectrons, thereby imaging a portion of the substrate, and
  a means (1006) for detecting electrons reflected from the surface of the substrate, with an additional sixth component:

a means (1007) for converting the reflected electrons to photons before they strike the detector.

The means (1007) for converting the photoelectrons to photons (thereby improving image quality) could consist of a scintillating material, a phosphorescent material, or any other material which will generate photons when struck by electrons.

Figure 11:
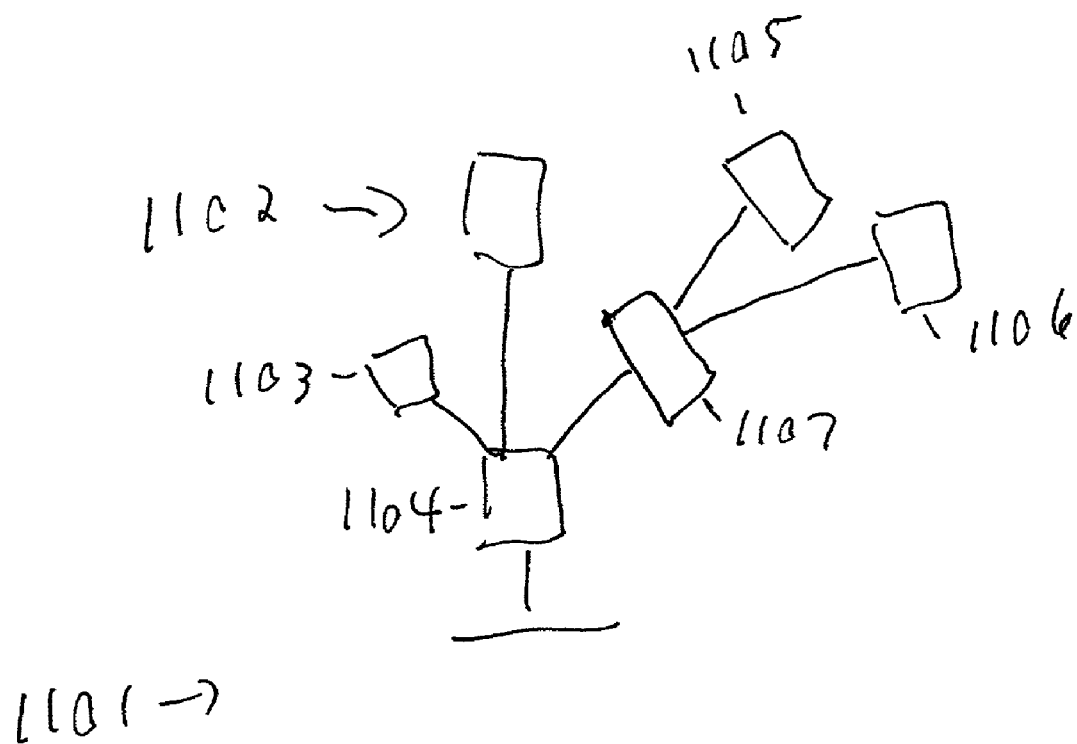
FIG. 11 shows a dual-beam photoelectron emission microscope which incorporates a means for selecting reflected electrons.

In the dual-beam photoelectron emission microscopes shown in FIGS. 9 and 10, the means (906 and 1006) for detecting reflected electrons detects photoelectrons as well as reflected electrons. FIG. 11 shows an embodiment of the invention which creates images based preferentially on reflected electrons. It contains the five components shown in FIG. 9:

a means (1102) for exposing the substrate to an influx of photons with an energy sufficient to cause photoelectrons to leave the surface of the substrate,
  a means (1103) for exposing the substrate to an influx of electrons which have both an energy and a current density profile selected to maintain the surface charge present on the substrate at a predetermined level,
  electron optics (1104) for focusing the photoelectrons in the plane of a detector,
  a means (1105) for detecting the photoelectrons, thereby imaging a portion of the substrate, and
  a means (1106) for detecting electrons reflected from the surface of the substrate, with an additional sixth component:

a means (1107) for selecting said most or all of the reflected electrons, or a portion of the reflected electrons, and rejecting most or all of the photoelectrons emitted from the substrate.

Figure 12:
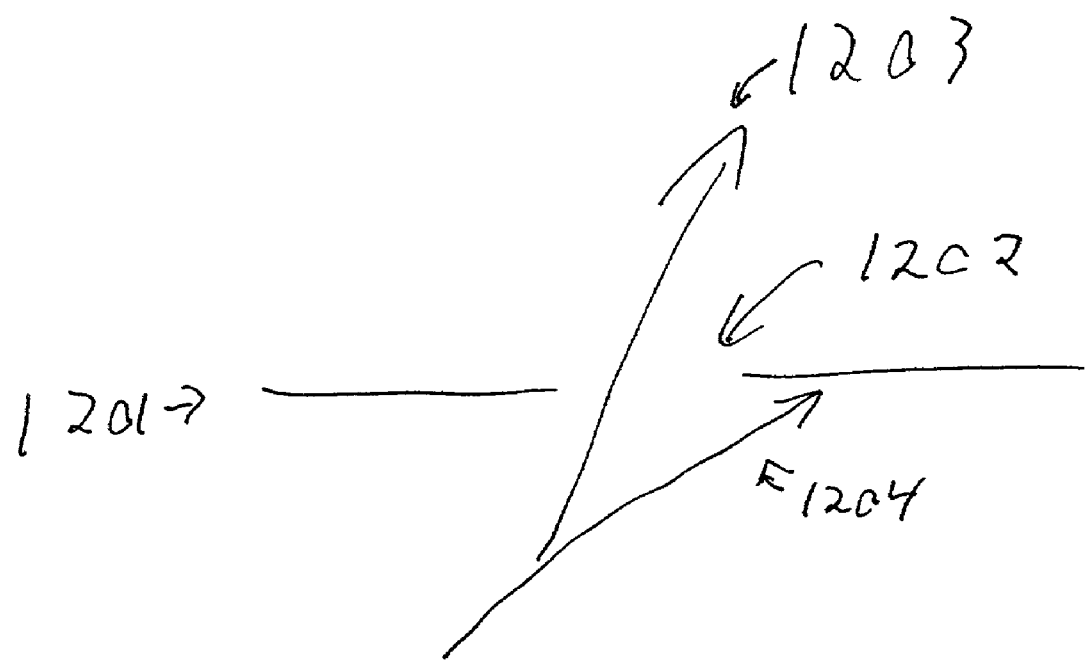
FIG. 12 shows a filter for selecting reflected electrons and rejecting photoelectrons.

This sixth component can consist of a filter which selects reflected electrons and rejects photoelectrons based on their angular distribution. FIG. 12 shows one specific example of such a filter 1201, a blocking means containing a shaped aperture 1202. As explained above with reference to FIG. 8, the filter can select reflected electrons 1203 and reject photoelectrons 1204 based on their angular distribution because the reflected electrons have the peak of their distribution at an angle of reflection which equals their angle of incidence, and the photoelectrons have the peak of their distribution normal to the substrate.

Having completed our disclosure of innovative hardware for dual-beam photoelectron emission microscopes, we now describe novel methods of applying those systems, first by detecting primarily photoelectrons, then by detecting primarily reflected electrons, and finally by detecting both photoelectrons and reflected electrons.

Figure 13:
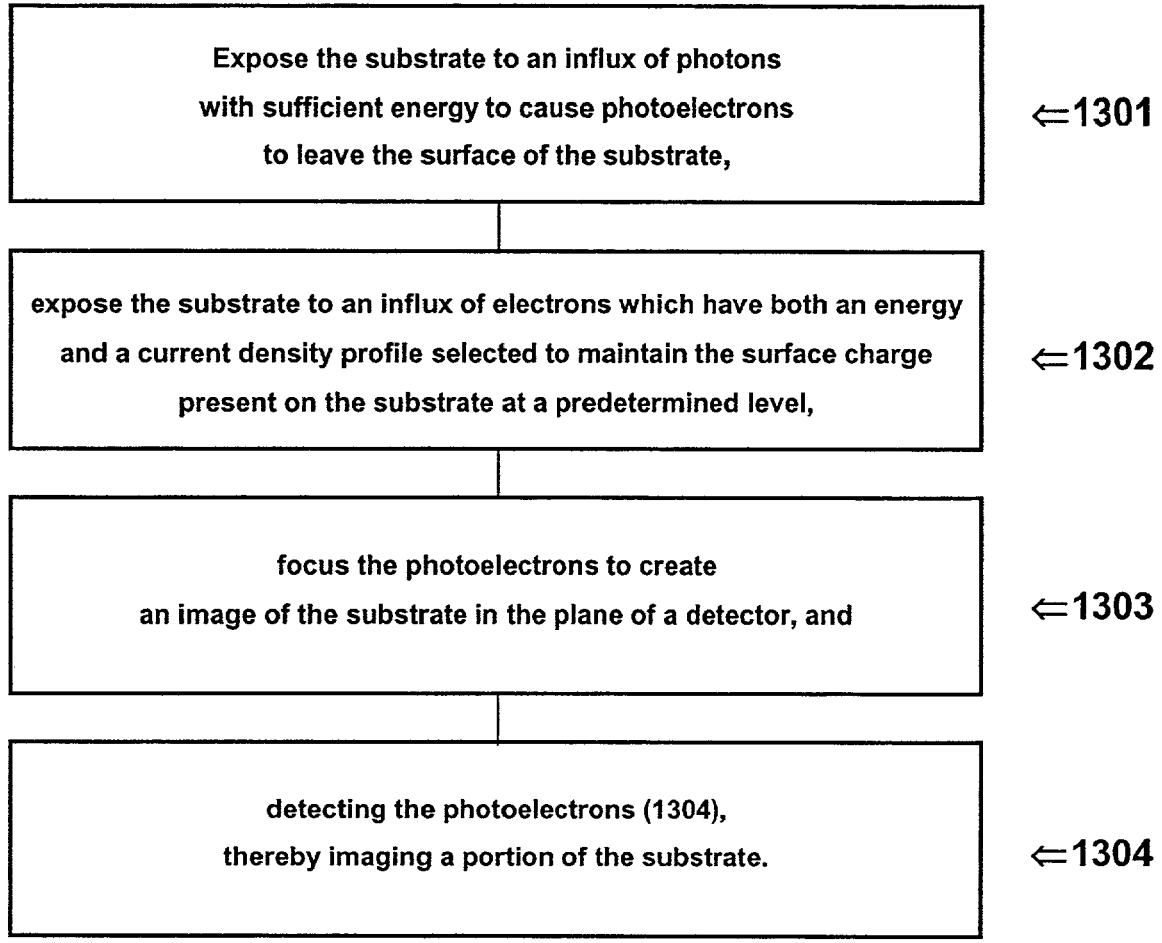
FIG. 13 illustrates a novel method of imaging a substrate with a dual-beam photoelectron emission microscope by detecting photoelectrons.

Methods of Imaging a Substrate with a Dual-Beam Photoelectron Emission Microscope by Detecting Photoelectrons FIG. 13 illustrates a novel method of imaging a substrate with a dual-beam photoelectron emission microscope by detecting photoelectrons. It includes the following steps:

exposing the substrate to an influx of photons with sufficient energy to cause photoelectrons to leave the surface of the substrate (1301), exposing the substrate to an influx of electrons which have both an energy and a current density profile selected to maintain the surface charge present on the substrate at a predetermined level (1302), focusing the photoelectrons to create an image of the substrate in the plane of a detector (1303), and detecting the photoelectrons (1304), thereby imaging a portion of the substrate.

The novelty of this step lies in step (1302), where an electron beam prevents the accumulation of a strong positive charge on the substrate.

In an important variant of this method, at least two materials are visible on the surface of the substrate, and the photons which strike the surface have an energy selected to increase the difference in photoelectron yield between at least two of the materials. An earlier section gave the example of choosing a photon energy between the work function of aluminum and the work function of silicon in order to increase image contrast; that example applies here as well.

In other variants of the method shown in FIG. 13, it is possible to expose the substrate to the influx of photons and the influx of electrons either concurrently or alternately.

In yet another variant of the method shown in FIG. 13, it is possible to limit the accumulation of positive charge on the wafer most effectively by exposing the substrate to electrons over a relatively large area and to photons over a relatively small area confined within the larger area exposed to electrons.

Figure 14:
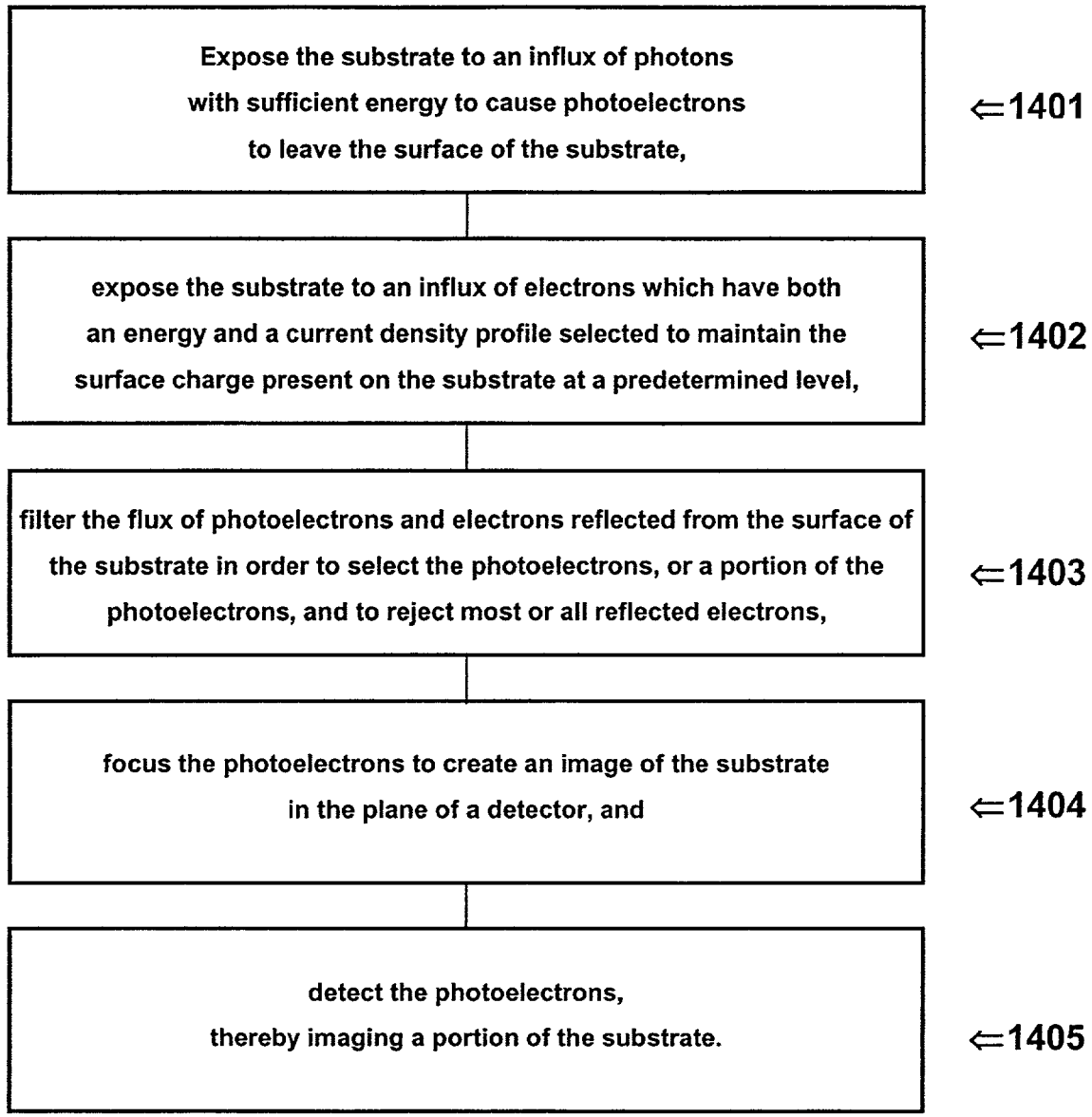
FIG. 14 illustrates a method of imaging a substrate with a dual-beam photoelectron emission microscope which involves filtering the flux of photoelectrons and electrons reflected from the surface of the substrate in order to select the photoelectrons.

The method shown in FIG. 13 may detect some reflected electrons (i.e., electrons in the charge control beam reflected from the surface of the substrate) as well as photoelectrons. To produce an image with optimal contrast between different materials, it will be useful to maximize the percentage of photoelectrons and minimize the percentage of reflected electrons which strike the detector. To this end, we disclose the method shown in FIG. 14:

exposing the substrate to an influx of photons with sufficient energy to cause photoelectrons to leave the surface of the substrate (1401), exposing the substrate to an influx of electrons which have both an energy and a current density profile selected to maintain the surface charge present on the substrate at a predetermined level (1402), filtering the flux of photoelectrons and electrons reflected from the surface of the substrate in order to select the photoelectrons, or a portion of the photoelectrons, and to reject most or all reflected electrons (1403), focusing the photoelectrons to create an image of the substrate in the plane of a detector (1404), and detecting the photoelectrons (1405), thereby imaging a portion of the substrate, One preferred method of achieving the filtering step (1403) is to filter the flux of photoelectrons and reflected electrons based on their angular distribution from the surface, as discussed above with reference to FIG. 8.

In yet another variant of the method shown in FIG. 13, the surface of the substrate is made up of at least two materials, and the photons which strike the surface have an energy selected to increase the difference in photoelectron yield between at least two of the materials, as described earlier. In yet another variant of the method shown in FIG. 13, it is possible to direct the influx of photons on the substrate at a 90 degree angle for some imaging modes or at some smaller angle for other imaging modes, as described earlier. Likewise, it can be useful to polarize the influx of photons either vertically or horizontally. An explanation of why these variants are useful appears above in the section on Methods of Imaging and Inspecting Wafers or Reticles with a Single-Beam Photoelectron Emission Microscope.

Figure 15:
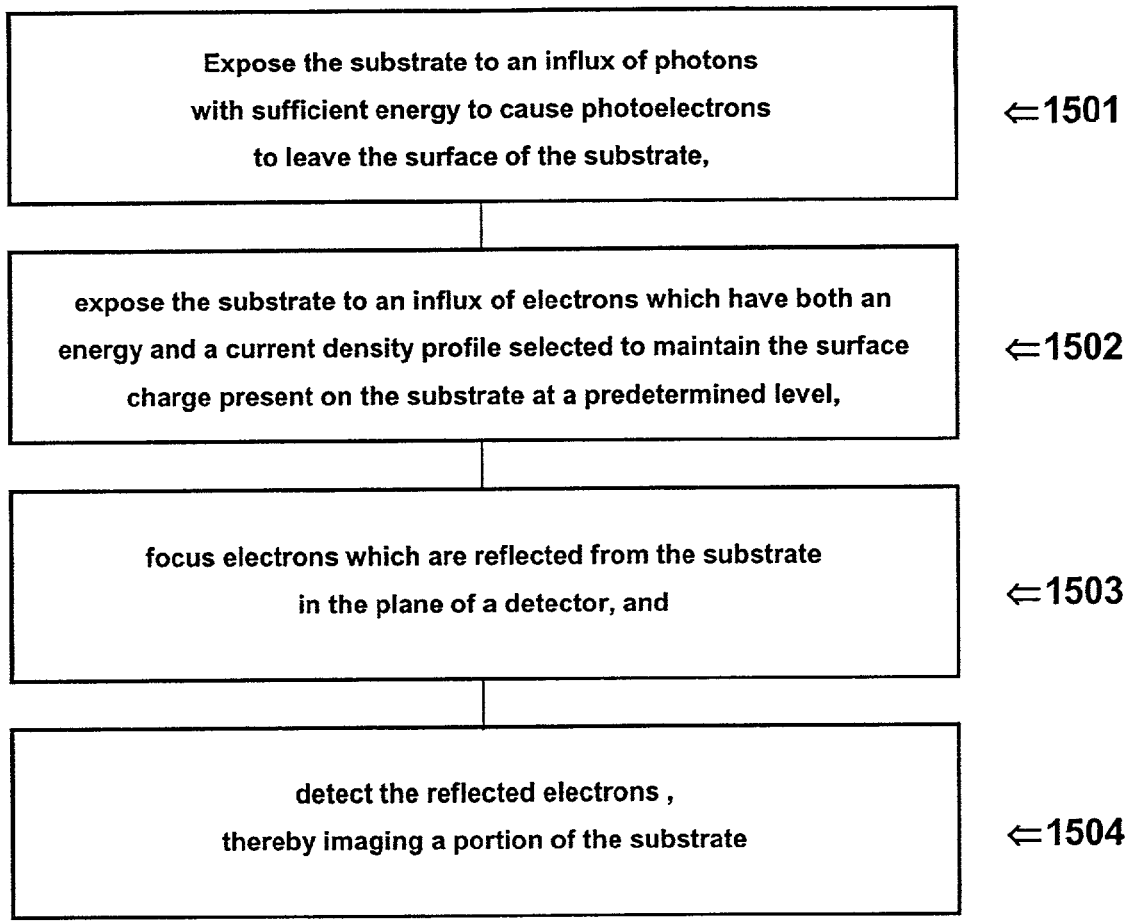
FIG. 15 illustrates a novel method of imaging a substrate with a dual-beam photoelectron emission microscope by detecting reflected electrons.

Methods of Imaging a Substrate with a Dual-Beam Photoelectron Emission Microscope by Detecting Reflected Electrons FIG. 15 illustrates a novel method of imaging a substrate with a dual-beam photoelectron emission microscope by detecting reflected electrons. It includes the following steps:

exposing the substrate to an influx of photons with sufficient energy to cause photoelectrons to leave the surface of the substrate (1501), exposing the substrate to an influx of electrons which have both an energy and a current density profile selected to maintain the surface charge present on the substrate at a predetermined level (1502), focusing electrons which are reflected from the substrate in the plane of a detector (1503), and detecting the reflected electrons (1504), thereby imaging a portion of the substrate.

The novelty of this method lies in steps (1503) and (1504), using a dual-beam photoemission electron microscope to create an image from electrons in the charge control beam which are reflected by the substrate. This image can be extremely sensitive to topography.

In variants of the method shown in FIG. 15, it is possible to expose the substrate to the influx of photons and the influx of electrons either concurrently or alternately.

In yet another variant of the method shown in FIG. 15, it is possible to limit the accumulation of positive charge on the wafer effectively by exposing the substrate to electrons over a relatively large area and to photons over a relatively small area confined within the larger area exposed to electrons.

Figure 16:
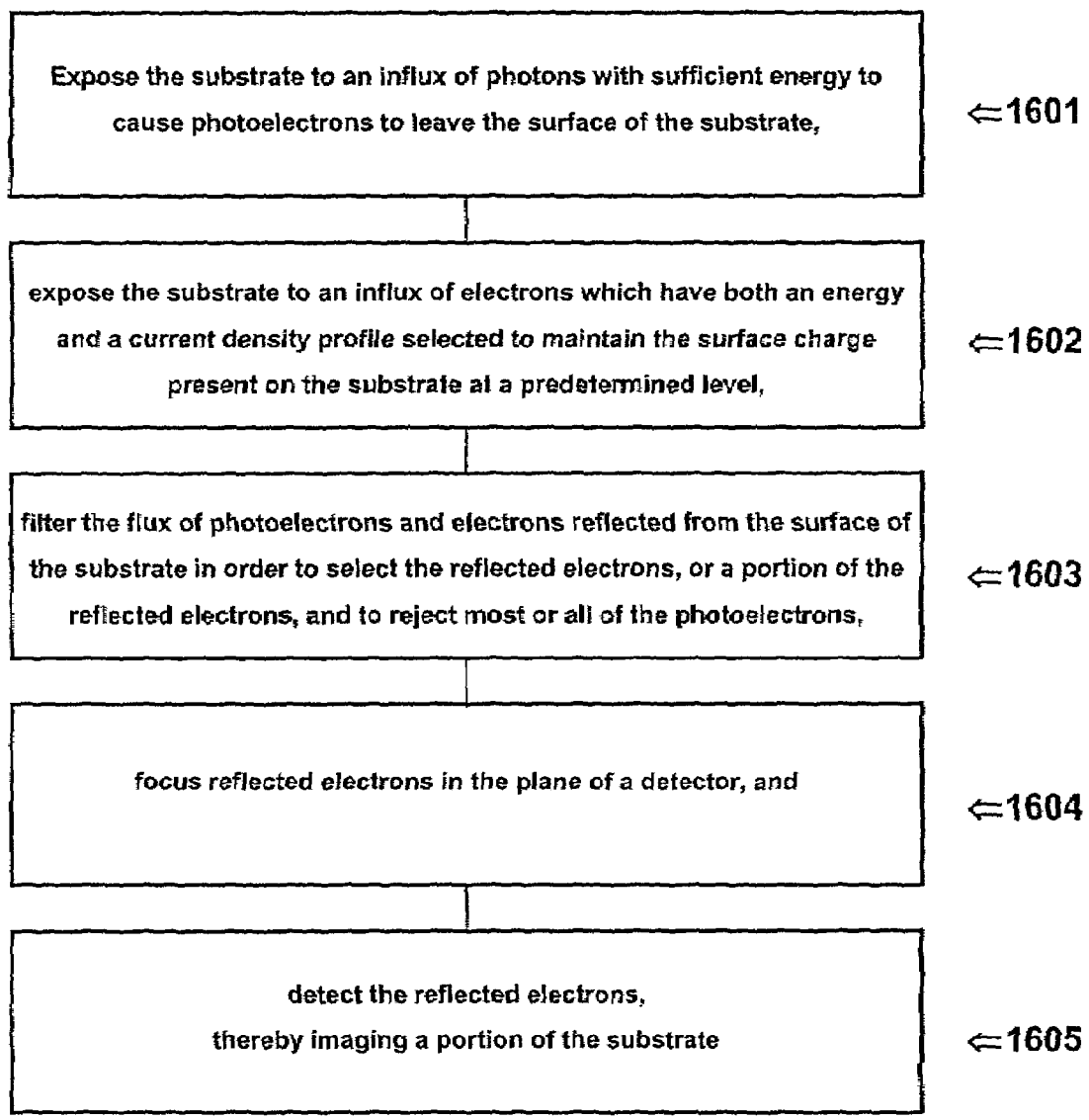
FIG. 16 illustrates a method of imaging a substrate with a dual-beam photoelectron emission microscope which involves filtering the flux of photoelectrons and electrons reflected from the surface of the substrate in order to select the reflected electrons.

The method shown in FIG. 15 may detect some photoelectrons as well as reflected electrons. To produce an image with optimal sensitivity to topography, it will be useful to maximize the percentage of reflected electrons and minimize the percentage of photoelectrons which strike the detector. To this end, we disclose the method shown in FIG. 16:

exposing the substrate to an influx of photons with sufficient energy to cause photoelectrons to leave the surface of the substrate (1601), exposing the substrate to an influx of electrons which have both an energy and a current density profile selected to maintain the surface charge present on the substrate at a predetermined level (1602), filtering the flux of photoelectrons and electrons reflected from the surface of the substrate in order to select the reflected electrons, or a portion of the reflected electrons, and to reject most or all of the photoelectrons (1603), focusing reflected electrons in the plane of a detector (1604), and detecting the reflected electrons (1605), thereby imaging a portion of the substrate.

One preferred method of carrying out the filtering in step (1603) is to select the reflected electrons, or a portion of the reflected electrons, based on their angular distribution from the surface of the substrate. As explained above, the reflected electrons have their peak of distribution at a specular angle (i.e., at an angle of reflection which equals their angle of incidence), whereas the photoelectrons have their peak of distribution normal to the substrate.

In a variation of the method described in the previous paragraph, the filtering rejects most or all of the reflected electrons which are reflected at or near the specular angle and selects most or all reflected electrons which are scattered away from the specular angle. This method gives high sensitivity to particles or other contamination defects on the surface which scatter incoming electrons.

Figure 17:
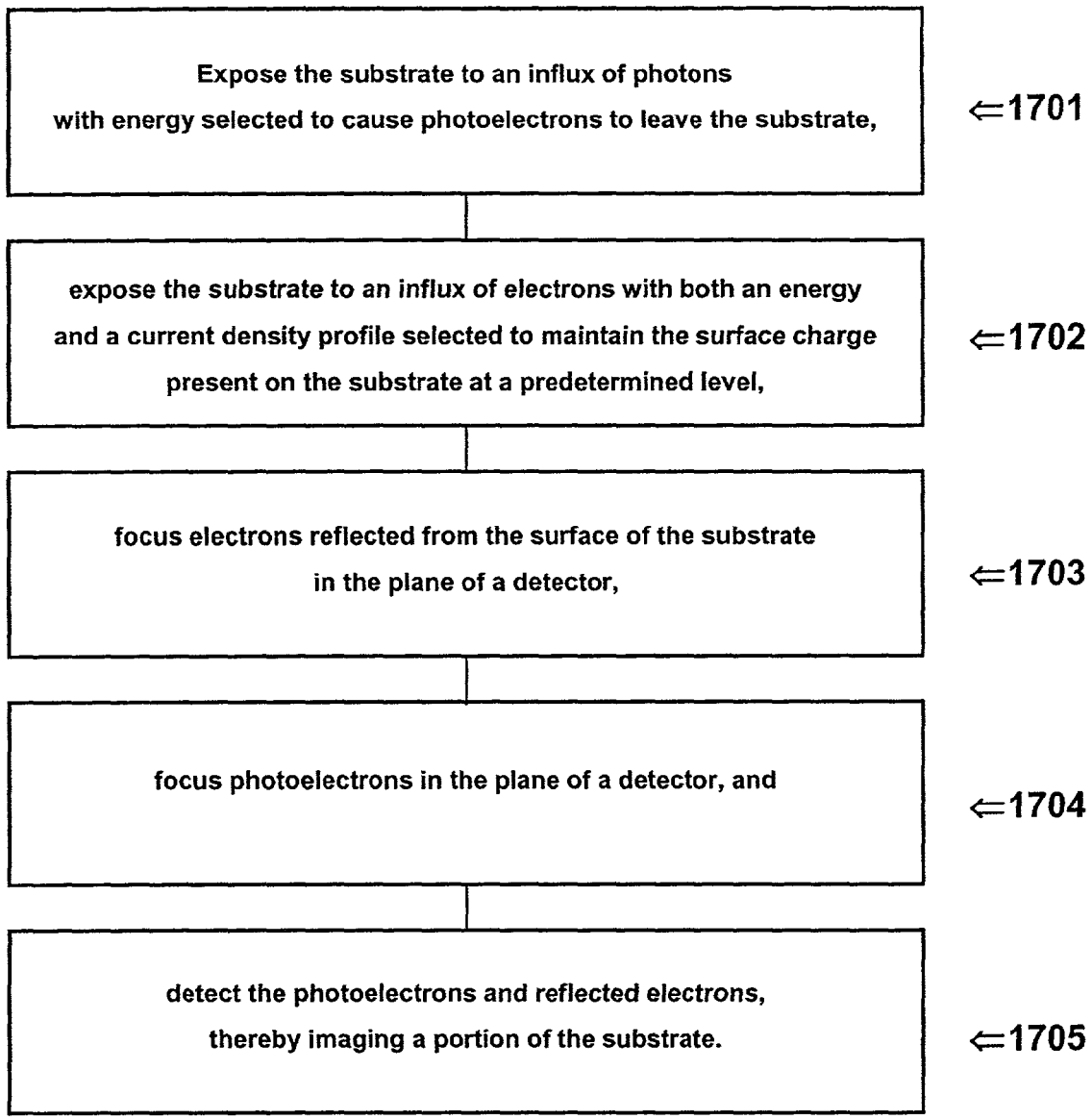
FIG. 17 illustrates a novel method of imaging a substrate with a dual-beam photoelectron emission microscope by detecting both reflected electrons and photoelectrons.

Methods of Imaging a Substrate with a Dual-Beam Photoelectron Emission Microscope by Detecting Both Photoelectrons and Reflected Electrons FIG. 17 illustrates a novel method of imaging a substrate with a dual-beam photoelectron emission microscope by detecting both photoelectrons and reflected electrons. It includes the following steps:

exposing the substrate to an influx of photons with energy selected to cause photoelectrons to leave the substrate (1701), exposing the substrate to an influx of electrons with both an energy and a current density profile selected to maintain the surface charge present on the substrate at a predetermined level (1702), focusing electrons reflected from the surface of the substrate in the plane of a detector (1703), focusing photoelectrons in the plane of a detector (1704), and detecting the photoelectrons and reflected electrons (1705), thereby imaging a portion of the substrate.

In a variation of the method shown in FIG. 17, it can be useful to position the filter so that it increases sensitivity to defects and decreases sensitivity to non-defective parts of the surface. Areas on the substrate which are free of particle contamination tend to reflect electrons at or near the specular angle and to emit photoelectrons at an angle perpendicular to the substrate. To decrease sensitivity to those areas, it is useful to position a filter so that it rejects most or all of the reflected electrons which are reflected at or near the specular angle and most or all of the photoelectrons which are emitted perpendicular to the surface of the substrate. On the other hand, particles and other contamination defects tend to scatter reflected electrons away from the specular angle and to emit photoelectrons at angles other than perpendicular to the substrate. To increase sensitivity to those defects, it is useful to position the filter so that it selects most or all of the reflected electrons which are scattered away from the specular angle and most or all of the photoelectrons which are emitted at angles other than perpendicular to the surface. Under these circumstances, the image will offer excellent contrast for contamination defects, which will appear white against a dark background.

Figure 18:
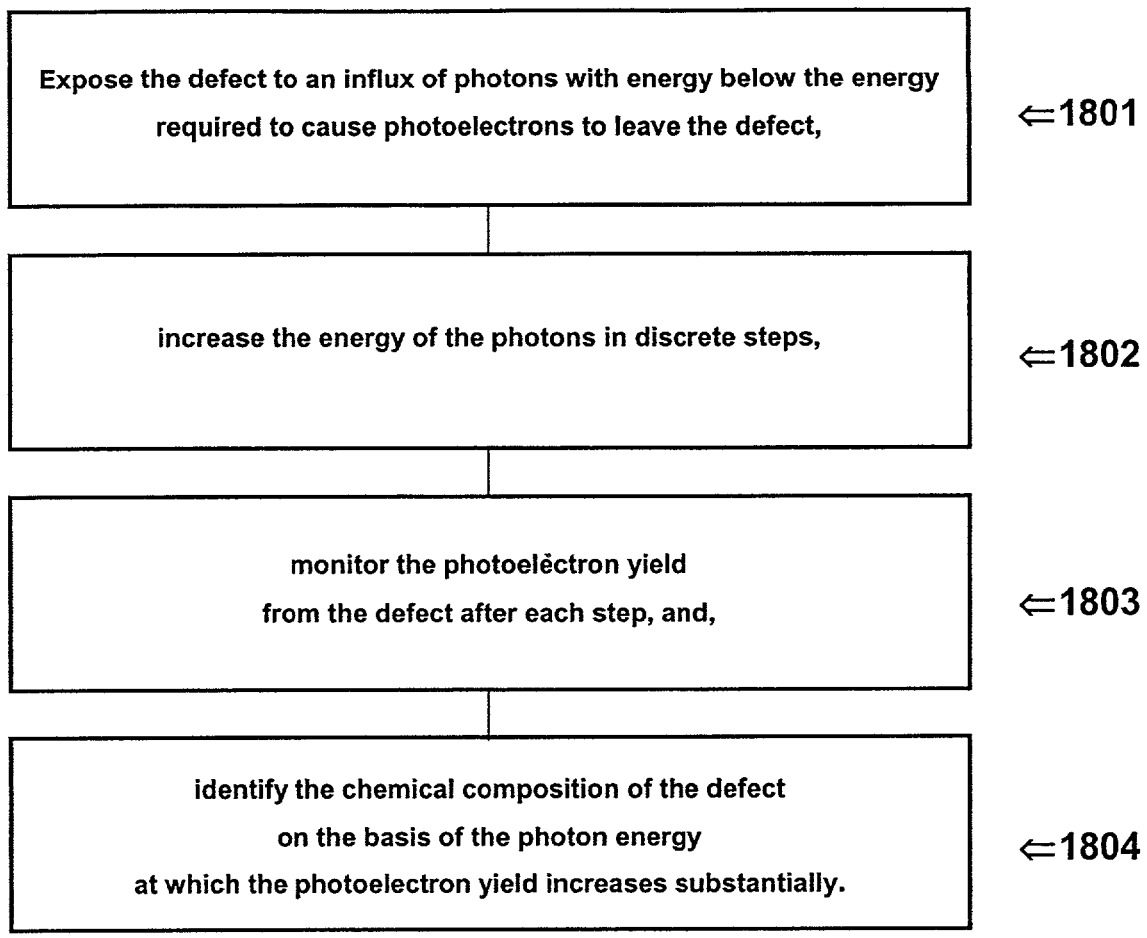
FIG. 18 illustrates a novel method of identifying the chemical composition of a defect on a wafer or a reticle.

Methods of Identifying the Chemical Composition of a Defect with a Photoelectron Emission Microscope A photoelectron emission microscope for inspecting substrates gives a new capability: a method of identifying the chemical composition of a defect. In a wafer fab or a mask shop, this capability can help engineers to identify the source of a defect so they can quickly correct a yield-limiting problem. FIG. 18 illustrates this method:

exposing the defect to an influx of photons with energy below the energy required to cause photoelectrons to leave the defect (1801), increasing the energy of the photons in discrete steps (1802), monitoring the photoelectron yield from the defect after each step (1803), and identifying the chemical composition of the defect on the basis of the photon energy at which the photoelectron yield increases substantially (1804).

The photoelectron yield will increase substantially when the energy of the photons reaches the work function of the material from which the defect is made. The value of that energy provides a clue to the chemical makeup of the defect because the work functions of materials used in semiconductor manufacturing are widely known.

The novel apparati and methods we have described for filtering photoelectrons and reflected electrons in a photoemission electron microscope are also novel and useful when applied to inspection of substrates with a dual-beam electron microscope. We will now disclose those inventions.

Figure 19:
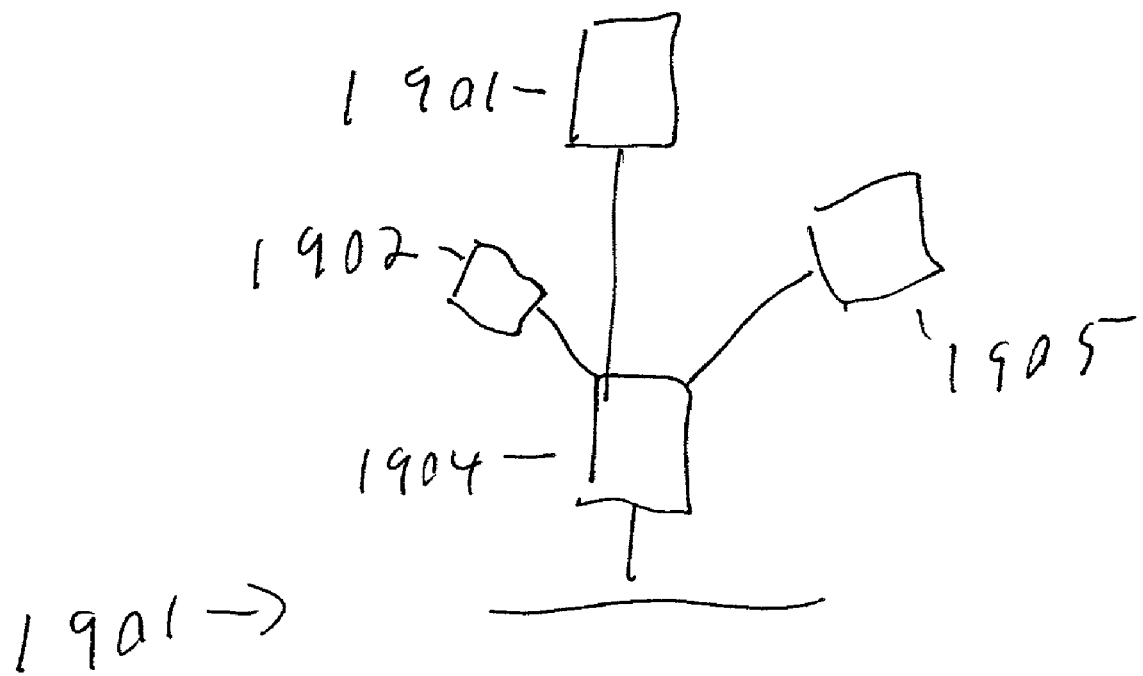
FIG. 19 shows a dual-beam secondary electron emission microscope for imaging substrates primarily with secondary electrons.

Dual-Beam Secondary Electron Emission Microscope for Imaging Substrates Primarily with Secondary Electrons FIG. 19 shows a dual-beam secondary electron emission microscope (1901) for imaging substrates primarily with secondary electrons. It includes the following components:

means (1902) for exposing the substrate to an influx of relatively high-energy electrons, with energy selected to cause secondary electrons to leave the substrate, means (1903) for exposing the substrate to an influx of relatively low-energy electrons, with both an energy and a current density profile selected to maintain surface charge present on the substrate at a predetermined level, means (1904) for selecting most or all of the secondary electrons, or a portion of the secondary electrons, and rejecting most or all of the relatively low-energy electrons reflected from the substrate, and means (1905) for detecting the secondary electrons, thereby imaging a portion of said substrate.

Figure 20:
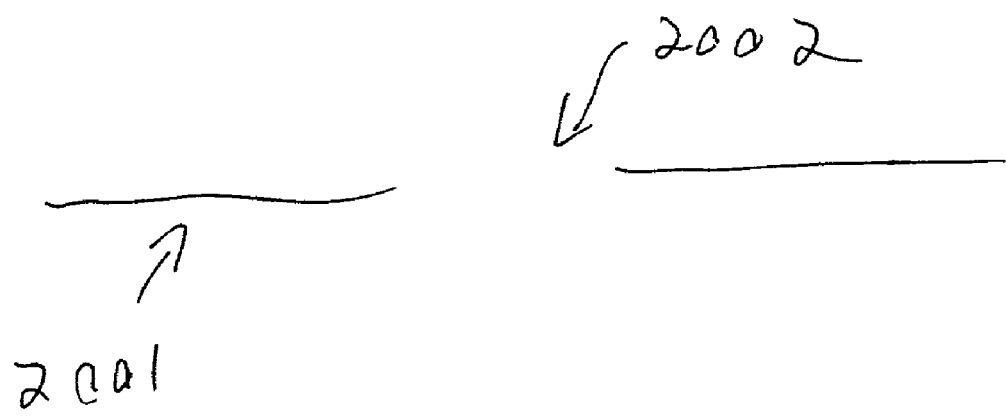
FIG. 20 illustrates a filter which selects secondary electrons and rejects reflected electrons based on their angular distributions.

The novelty of the invention shown in FIG. 19 lies in (1904), the means for selecting secondary electrons and rejecting reflected electrons. This means (1904) can consist of a filter which selects most or all of the secondary electrons and rejects most or all of the reflected electrons based on their angular distributions. FIG. 20 shows one possible embodiment of this filter, a blocking means 2001 containing an aperture 2002.

Figure 21:
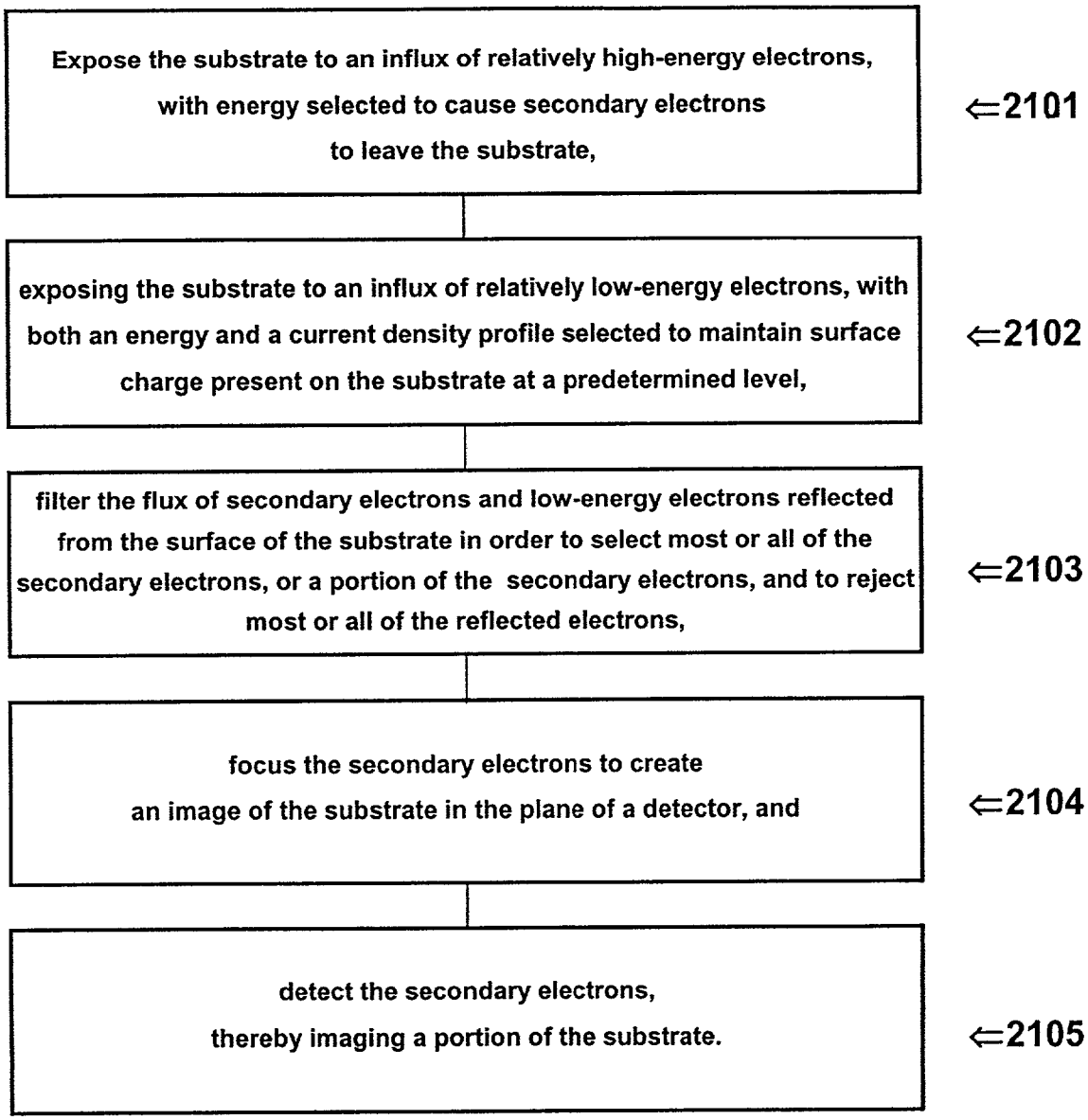
FIG. 21 illustrates a novel method of imaging a substrate with a dual-beam secondary electron emission microscope.

Methods of Imaging a Substrate with a Dual-Beam Secondary Electron Emission Microscope by Detecting Photoelectrons FIG. 21 illustrates a novel and useful method of imaging a substrate with a dual-beam secondary electron emission microscope. It includes the following five steps:

exposing the substrate to an influx of relatively high-energy electrons, with energy selected to cause secondary electrons to leave the substrate (2101), exposing the substrate to an influx of relatively low-energy electrons, with both an energy and a current density profile selected to maintain surface charge present on the substrate at a predetermined level (2102), filtering the flux of secondary electrons and low-energy electrons reflected from the surface of the substrate in order to select most or all of the secondary electrons, or a portion of the secondary electrons, and to reject most or all of the reflected electrons (2103), focusing the secondary electrons to create an image of the substrate in the plane of a detector (2104), and detecting the secondary electrons, thereby imaging a portion of the substrate (2105).

The novelty of this method lies in step (2103), filtering the flux of secondary electrons and reflected electrons to select secondary electrons and reject reflected electrons. One preferred method of filtering the flux (2103) is to select the secondary electrons, or a portion of the secondary electrons, based on their angular distribution from the surface of the substrate. This method is possible is because the secondary electrons (like the photoelectrons in a photoelectron emission microscope) have the peak of their distribution normal to the surface of the substrate. The reflected electrons have the peak of their distribution at an angle of reflection which equals their angle of incidence.

Figure 22:
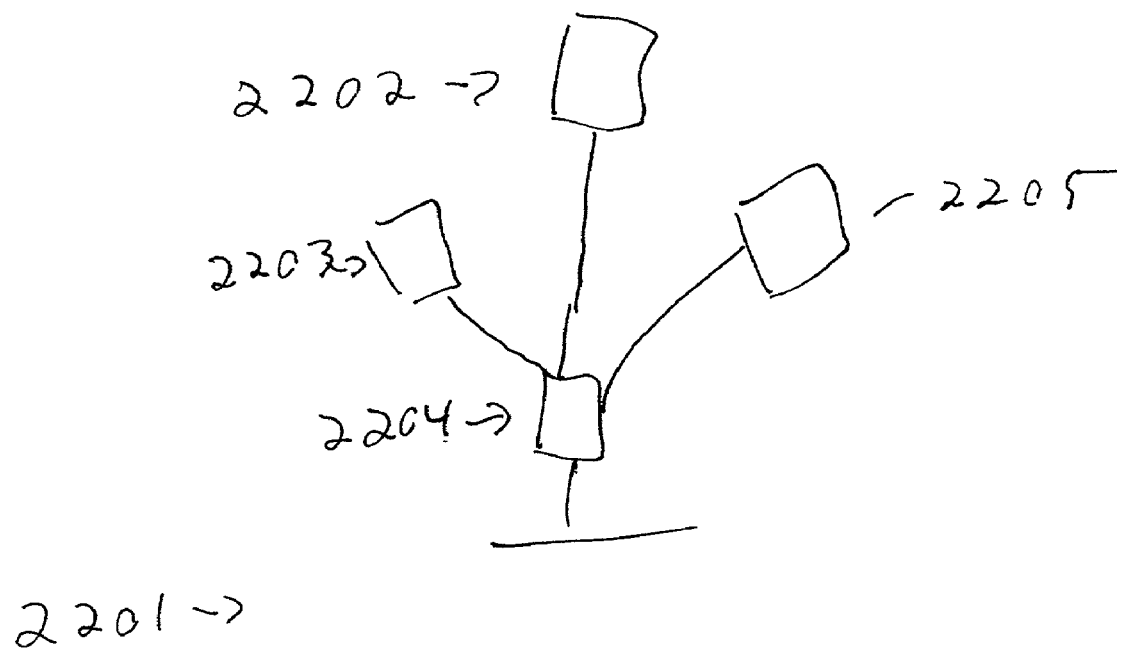
FIG. 22 shows a dual-beam secondary electron emission microscope for imaging substrates primarily with reflected electrons.

Dual-Beam Secondary Electron Emission Microscope for Imaging Substrates Primarily with Reflected Electrons FIG. 22 shows a dual-beam secondary electron emission microscope (2201) for imaging substrates primarily with reflected electrons. It includes the following components:

means (2202) for exposing the substrate to an influx of relatively high-energy electrons, with energy selected to cause secondary electrons to leave the substrate, means (2203) for exposing said substrate to an influx of relatively low-energy electrons, with both an energy and a current density profile selected to maintain surface charge present on the substrate at a predetermined level, means (2204) for selecting most or all of the relatively low-energy electrons reflected from the substrate, or a portion of those reflected electrons, and rejecting most or all of the secondary electrons, and means (2205) for detecting the reflected electrons, thereby imaging a portion of said substrate.

Figure 23:
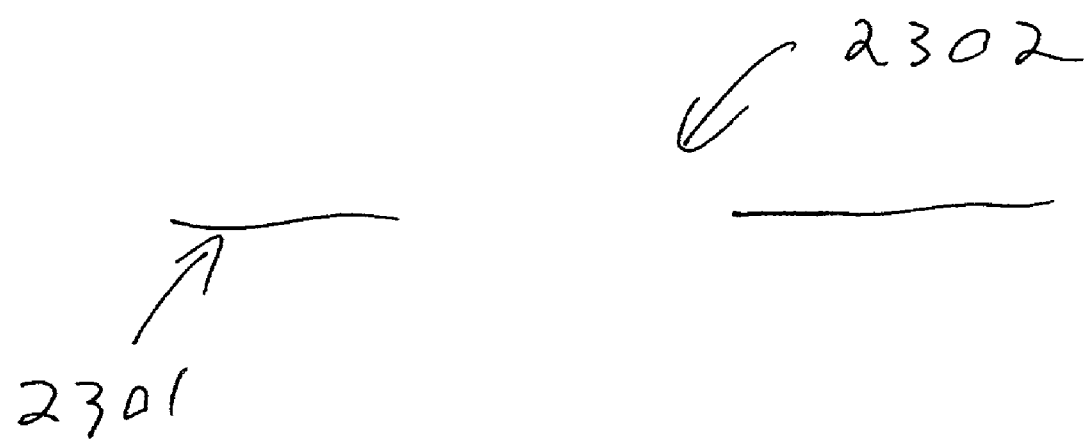
FIG. 23 shows a filter which can select reflected electrons and reject secondary electrons based on their angular distributions.

The novelty of the invention shown in FIG. 22 lies in (2204), the means for selecting reflected electrons and rejecting secondary electrons. This means (2204) can consist of a filter which selects most or all of the reflected electrons and rejects most or all of the secondary electrons based on their angular distributions. FIG. 23 shows one possible embodiment of this filter, a blocking means 2301 containing an aperture 2302.

Figure 24:
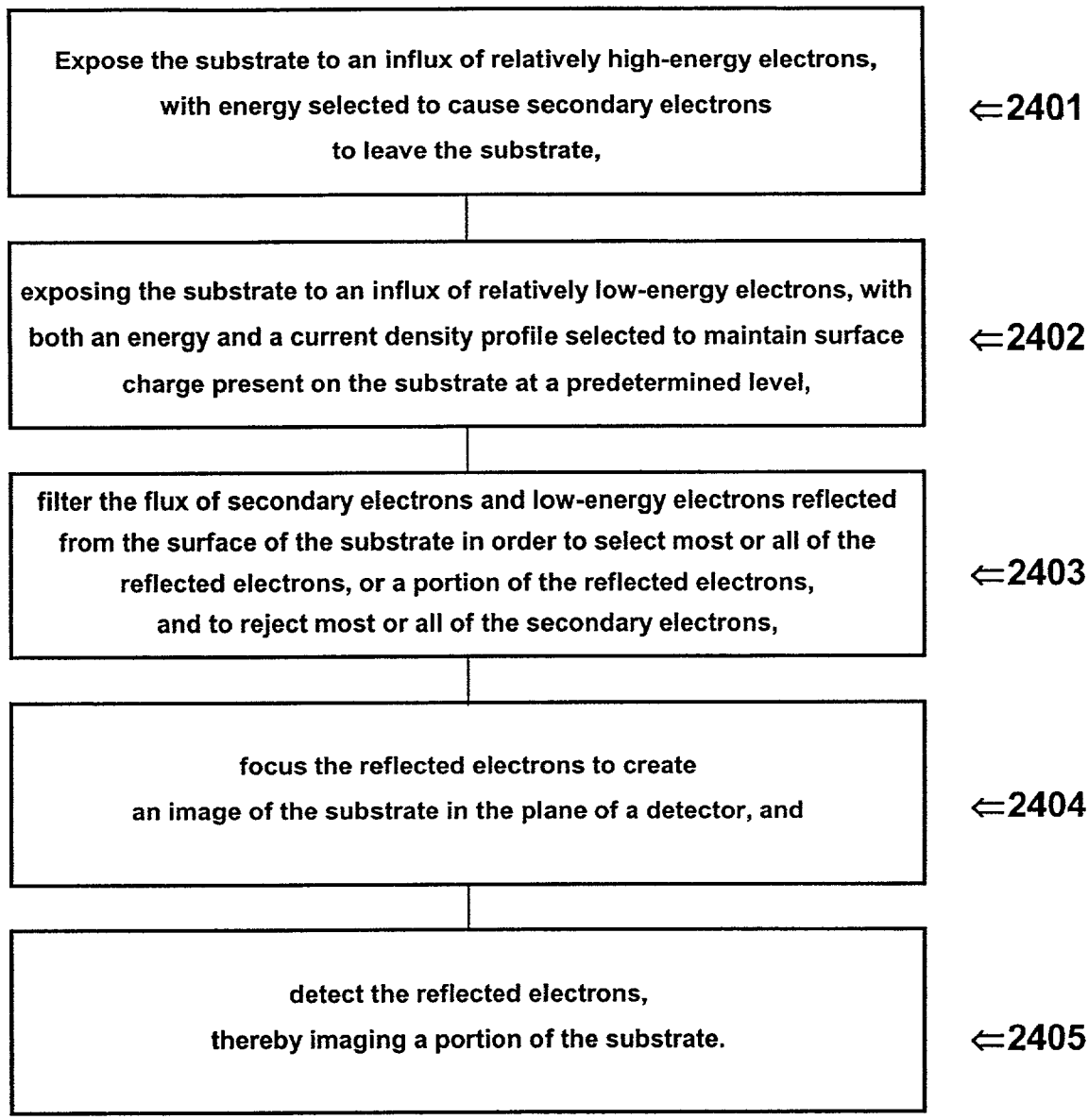
FIG. 24 illustrates a novel and useful method of imaging a substrate with a dual-beam secondary electron emission microscope by detecting reflected electrons.

Methods of Imaging a Substrate with a Dual-Beam Secondary Electron Emission Microscope by Detecting Reflected Electrons FIG. 24 illustrates a novel and useful method of imaging a substrate with a dual-beam secondary electron emission microscope by detecting reflected electrons. It includes the following five steps:

exposing the substrate to an influx of relatively high-energy electrons, with energy selected to cause secondary electrons to leave the substrate (2401), exposing the substrate to an influx of relatively low-energy electrons, with both an energy and a current density profile selected to maintain surface charge present on the substrate at a predetermined level (2402), filtering the flux of secondary electrons and low-energy electrons reflected from the surface of the substrate in order to select most or all of the reflected electrons, or a portion of the reflected electrons, and to reject most or all of the secondary electrons (2403), focusing the reflected electrons to create an image of the substrate in the plane of a detector (2404), and detecting the reflected electrons, thereby imaging a portion of the substrate (2405).

The novelty of this method lies in step (2403), filtering the flux of reflected electrons and secondary electrons to select reflected electrons and reject secondary electrons. One preferred method of filtering the flux (2403) is to select the reflected electrons, or a portion of the reflected electrons, based on their angular distribution from the surface of the substrate. This method is possible because the reflected electrons have the peak of their distribution at an angle of reflection which equals the angle of incidence. The secondary electrons (like the photoelectrons in a photoelectron emission microscope) have the peak of their distribution normal to the surface of the substrate.

A different way to filter the reflected electrons based on their angular distribution is to reject most or all of the reflected electrons which are reflected at or near the specular angle and to select most or all of the reflected electrons which are scattered away from the specular angle. This method delivers superior sensitivity to particles or other contamination defects which scatter electrons.

Figure 25:
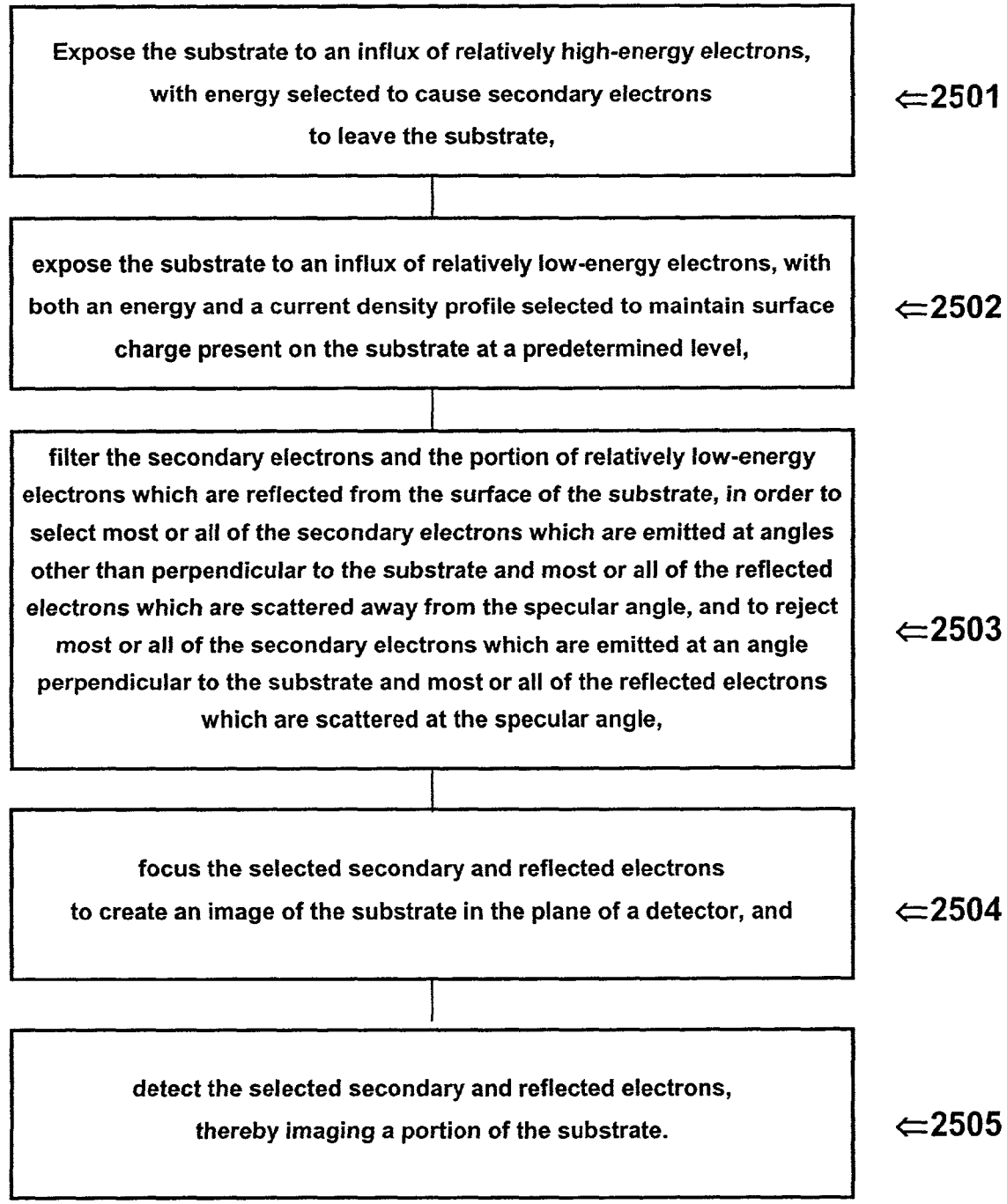
FIG. 25 illustrates a method of imaging a substrate with a dual-beam secondary electron emission microscope by detecting both secondary electrons and reflected electrons.

Method of Imaging a Substrate with a Dual-Beam Secondary Electron Emission Microscope by Detecting both Secondary Electrons and Reflected Electrons FIG. 25 illustrates a method of imaging a substrate with a secondary electron emission microscope by detecting both secondary and reflected electrons. The distinguishing feature of this method is to position the filter so that it increases sensitivity to defects and decreases sensitivity to non-defective parts of the surface. Areas on the substrate which are free of particle contamination tend to reflect incoming low-energy electrons at or near the specular angle and to emit secondary electrons at an angle perpendicular to the substrate. Therefore, it is possible to decrease sensitivity to those areas by positioning a filter so that it rejects electrons which are reflected at or near the specular angle and secondary electrons which are emitted perpendicular to the surface of the substrate. However, particles and other contamination defects tend to scatter reflected electrons away from the specular angle and to emit photoelectrons at angles other than perpendicular to the substrate. One can increase sensitivity to these defects by positioning the filter so that it selects reflected electrons which are scattered away from the specular angle and photoelectrons which are emitted at angles other than perpendicular to the surface. The contamination defects will then appear white against a dark background in the acquired image.

In total, the method includes the following steps:

exposing the substrate to an influx of relatively high-energy electrons with an energy selected to cause secondary electrons to leave the substrate (2501), exposing the substrate to an influx of relatively low-energy electrons with both an energy and a current density profile selected to maintain surface charge present on the substrate at a predetermined level (2502), filtering the secondary electrons and the portion of relatively low-energy electrons which are reflected from the surface of the substrate, in order to select most or all of the secondary electrons which are emitted at angles other than perpendicular to the substrate and most or all of the reflected electrons which are scattered away from the specular angle, and to reject most or all of the secondary electrons which are emitted at an angle perpendicular to the substrate and most or all of the reflected electrons which are scattered at the specular angle (2503), focusing the selected secondary and reflected electrons to create an image of the substrate in the plane of a detector (2504), detecting the selected secondary and reflected electrons, thereby imaging a portion of the substrate (2505).

The invention described herein is intended for the inspection of semiconductor wafers, photomasks, or other patterned or unpatterned substrates. More broadly, it can be applied to the imaging or inspection of any kind of substrate with a photoemission electron microscope or a secondary electron emission microscope. Although the invention has been described in relation to various implementations, together with modifications, variations, and extensions thereof, other implementations, modifications, variations and extensions are within the scope of the invention. Other embodiments may be apparent to those skilled in the art from consideration of the specification and invention disclosed herein. The invention is therefore not limited by the description contained herein or by the drawings, but only by the claims and their equivalents.

What is claimed is:

1. A method of imaging a substrate, comprising:
   a) exposing said substrate to an influx of relatively high-energy electrons, said high-energy electrons having an energy selected to cause secondary electrons to leave said substrate,
   b) exposing said substrate to an influx of relatively low-energy electrons, said electrons having both an energy and a current density profile selected to maintain surface charge present on said substrate at a predetermined level,
   c) filtering said secondary electrons and the portion of said relatively low-energy electrons which are reflected from the surface of said substrate, after proper selection of the angle of incidence for the electron beams, in order to select most or all of said secondary electrons which are emitted at angles other than perpendicular to the substrate and most or all of said reflected electrons which are scattered away from the specular angle, and to reject most or all of said secondary electrons which are emitted at an angle perpendicular to the substrate and most or all of said reflected electrons which are scattered at the specular angle,
   d) focusing said selected secondary electrons and said selected reflected electrons to create an image of said substrate in the plane of a detector,
   e) detecting said selected secondary electrons and said selected reflected electrons, thereby imaging a portion of said substrate.

* * * * *